(12) United States Patent
Blake et al.

(10) Patent No.: US 8,067,589 B2
(45) Date of Patent: *Nov. 29, 2011

(54) HETEROCYCLIC COMPOUNDS USEFUL IN TREATING DISEASES AND CONDITIONS

(75) Inventors: Tanisha D. Blake, Florissant, MO (US); Bruce C. Hamper, Kirkwood, MO (US); Wei Huang, Wildwood, MO (US); James R. Kiefer, Jr., Ballwin, MO (US); Joseph B. Moon, Saint Louis, MO (US); Bradley E. Neal, Saint Louis, MO (US); Kirk L. Olson, Canton, MI (US); Matthew J. Pelc, Ballwin, MO (US); Barbara A. Schweitzer, Webster Groves, MO (US); Atli Thorarensen, Dardenne Praire, MO (US); John I. Trujillo, Saint Charles, MO (US); Steven R. Turner, Labadie, MO (US)

(73) Assignee: Pfizer Inc, New York, NY (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/500,133

(22) Filed: Jul. 9, 2009

(65) Prior Publication Data

US 2009/0281125 A1    Nov. 12, 2009

Related U.S. Application Data

(63) Continuation of application No. 12/032,723, filed on Feb. 18, 2008, now Pat. No. 7,582,643.

(60) Provisional application No. 60/891,650, filed on Feb. 26, 2007.

(51) Int. Cl.
   *C07D 237/00* (2006.01)
   *C07D 401/00* (2006.01)
   *C07D 401/04* (2006.01)
   *A61K 31/505* (2006.01)

(52) U.S. Cl. ......... 544/224; 544/333; 514/256; 514/269

(58) Field of Classification Search ............... None
   See application file for complete search history.

(56) References Cited

U.S. PATENT DOCUMENTS

| | | | |
|---|---|---|---|
| 2005/0165028 A1 | 7/2005 | Norman et al. | 514/256 |
| 2005/0288286 A1 | 12/2005 | Flynn et al. | 514/235.2 |
| 2006/0100245 A1 | 5/2006 | Bakthavatchalam et al. | 514/332 |

FOREIGN PATENT DOCUMENTS

| | | |
|---|---|---|
| EP | 1217001 | 6/2002 |
| EP | 1471057 | 10/2004 |
| JP | 2004002248 | 1/2004 |
| JP | 2004051600 | 2/2004 |
| JP | 200751121 | 3/2007 |
| WO | WO9709315 | 3/1997 |
| WO | WO9736901 | 10/1997 |
| WO | WO9932454 | 7/1999 |
| WO | WO02066036 | 8/2002 |
| WO | WO03024448 | 3/2003 |
| WO | WO03051366 | 6/2003 |
| WO | WO2004006956 | 1/2004 |
| WO | WO2004031180 | 4/2004 |
| WO | WO2005003099 | 1/2005 |
| WO | WO2005028624 | 3/2005 |
| WO | WO2005040135 | 5/2005 |
| WO | WO2005072681 | 8/2005 |
| WO | WO2005094805 | 10/2005 |
| WO | WO2007007778 | 1/2007 |
| WO | WO2007041634 | 4/2007 |
| WO | WO2007042806 | 4/2007 |
| WO | WO2007048042 | 4/2007 |
| WO | WO2008075172 | 6/2008 |

OTHER PUBLICATIONS

Silverman, R., The Organic Chemistry of Drug Design and Drug Action, 2004, Elsevier, pp. 29-32.*
Hardman, J., ed. Goodman and Gilman's The Pharmacological Basis of Therapeutics, 9th ed., 1996 McGraw-Hill.*
Hcaplus 2004:1038664, "Preparation of substituted heterocycles for the treatment of abnormal cell growth," Bhattacharya et al., Dec. 2004.
J. Biol. Chem., 2006, 281(22), pp. 15277-15286.

* cited by examiner

*Primary Examiner* — Janet Andres
*Assistant Examiner* — Heidi Reese
(74) *Attorney, Agent, or Firm* — Jennifer A. Kispert; Robert T. Ronau

(57) ABSTRACT

The present invention relates to compounds of formula (I)

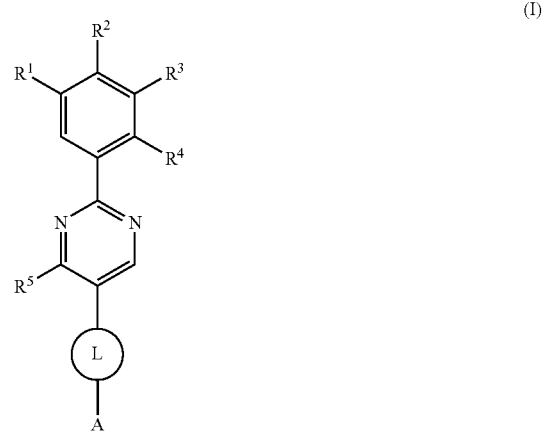

and pharmaceutically acceptable salts and solvates thereof, wherein the substituents are as defined herein, compositions containing such compounds and the uses of such compounds for the treatment of various diseases and conditions such as asthma.

5 Claims, No Drawings

HETEROCYCLIC COMPOUNDS USEFUL IN TREATING DISEASES AND CONDITIONS

This application is a Continuation of Ser. No. 12/032,723, filed Feb. 18, 2008, which claims the benefit of Provisional Patent Application No. 60/891,650, filed Feb. 26, 2007.

The present invention relates to pharmaceutically active compounds which are useful in the treatment of allergic and respiratory conditions and diseases. More particularly, the present invention relates to nicotinamide derivatives, and pharmaceutically acceptable salts and solvates thereof, and their use for treating prostaglandin $D_2$ mediated diseases including, but not limited to, allergic rhinitis, nasal congestion, rhinorrhea, perennial rhinitis, nasal inflammation, asthma of all types, chronic obstructive pulmonary diseases, allergic conjunctivitis, atopic dermatitis and other forms of lung inflammation. The invention also relates to pharmaceutical compositions comprising the nicotinamide derivatives.

Prostaglandin $D_2$ ($PGD_2$) is a metabolite of arachidonic acid. $PGD_2$ promotes sleep, inhibits platelet aggregation, relaxes smooth muscle contraction, induces bronchoconstriction and attracts inflammatory cells including Th2 cells, eosinophils and basophils. Both lipocalin-type PGD synthase (L-PGDS) and hematopoietic PGDS (H-PGDS) convert $PGH_2$ to $PGD_2$.

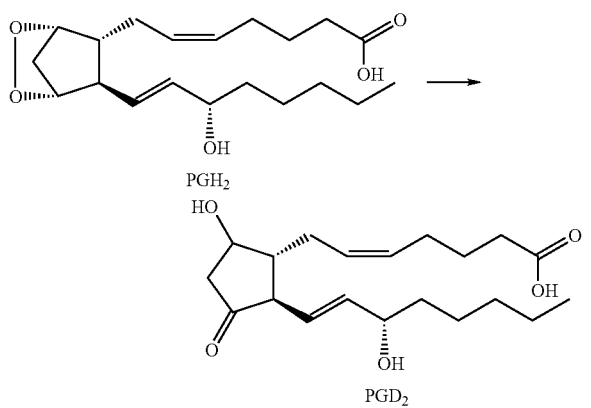

L-PGDS, also known as glutathione-independent PGDS or brain PGDS, is a 26 kDa secretory protein that is expressed by meningeal cells, epithelial cells of the choroid plexus and oligodendrocytes in the brain. L-PGDS secreted into cerebrospinal fluid is thought to be the source of $PGD_2$ in the central nervous system. In addition, epithelial cells in the epididymis and Leydig cells in the testis express L-PGDS and are thought to be the source of $PGD_2$ found in the seminal fluid. L-PGDS belongs to the lipocalin superfamily that consists of lipophilic ligand carrier proteins such as retinol- and retinoic acid-binding proteins.

In contrast, H-PGDS is a 26 kDa cytosolic protein that is responsible for the synthesis of $PGD_2$ in immune and inflammatory cells including mast cells, antigen-presenting cells and Th2 cells. H-PGDS is the only vertebrate member of the sigma class of glutathione S-transferases (GSTs). While both H- and L-PGDS convert $PGH_2$ to $PGD_2$, the mechanism of catalysis and specific activity of the enzymes are quite different.

The production of $PGD_2$ by H-PGDS is thought to play a pivotal role in airway allergic and inflammatory processes and induces vasodilatation, bronchoconstriction, pulmonary eosinophil and lymphocyte infiltration, and cytokine release in asthmatics. $PGD_2$ levels increase dramatically in bronchoalveolar lavage fluid following allergen challenge and the observation that patients with asthma exhibit bronchoconstriction upon inhalation of $PGD_2$ underscores the pathologic consequences of high levels of $PGD_2$ in the lung. Treatment with $PGD_2$ produces significant nasal congestion and fluid secretion in man and dogs, and $PGD_2$ is 10 times more potent than histamine and 100 times more potent than bradykinin in producing nasal blockage in humans, demonstrating a role for $PGD_2$ in allergic rhinitis.

Several lines of evidence suggest that PGDS is an excellent target for allergic and respiratory diseases or conditions. H-PGDS overexpressing transgenic mice show increased allergic reactivity accompanied by elevated levels of Th2 cytokines and chemokines as well as enhanced accumulation of eosinophils and lymphocytes in the lung. In addition, $PGD_2$ binds to two GPCR receptors, DP1 and CRTH2. Antigen-induced airway and inflammatory responses are strongly decreased in DP1-receptor null mice and recent evidence shows that $PGD_2$ binding to CRTH2 mediates cell migration and the activation of Th2 cells, eosinophils, and basophils in vitro and likely promotes allergic disease in vivo. Finally, several published reports link H-PGDS gene polymorphisms with atopic asthma. For example, Aritake et al., Structural and Functional Characterization of HQL-79, and Orally Selective inhibitor of Human Hematopoietic Prostaglandin D Synthase, *Journal of Biological Chemistry* 2006, 281(22), pp. 15277-15286, provides a rational basis for believing that inhibition of H-PGDS is an effective way of treating several allergic and non-allergic diseases.

Compounds have now been found that are effective for treating allergic and respiratory diseases. The compounds are inhibitors of H-PGDS, and at expected efficacious doses, do not significantly inhibit L-PGDS or kinases.

The invention therefore provides a compound of formula (I):

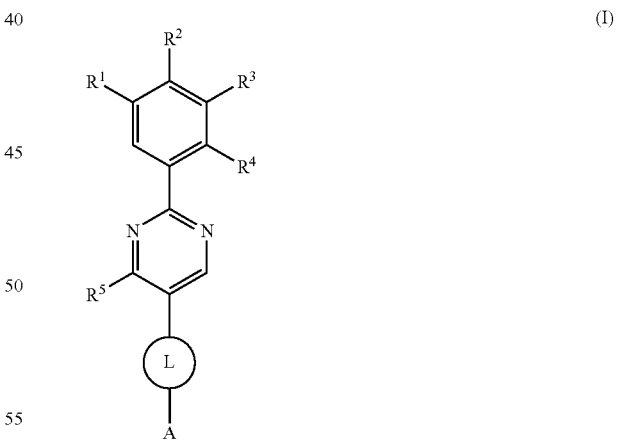

or a pharmaceutically acceptable salt or solvate thereof, wherein:

$R^1$, $R^3$ and $R^4$ are independently H, F, Cl, —$CHF_2$, —$CF_3$, —OH, —$CH_2OH$, —$CH_2CH_2OH$, —C≡N, —$CH_2$C≡N, —$CH_2CH_2$C≡N, $C_1$-$C_5$ alkyl, —C(O)$OR^{16}$, —NC(O)$R^{16}$, —$NSO_2R^{16}$, —C(O)$R^{16}$ or —$OCH_3$;

$R^2$ is H or F;

$R^5$ is H, —$NH_2$, —OH or —$CH_3$;

$R^{16}$ is $C_1$-$C_5$ alkyl;

L is —C(O)NH—, —NHC(O)— or —$CH_2$NHC(O)—;

A is:

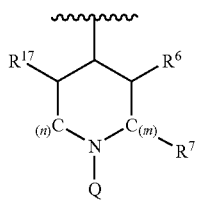

wherein: n is 0 or 1;
m is 0 or 1;
$R^6$ is H or OH and $R^{17}$ is H, or $R^6$ and $R^{17}$ form a bridge across the ring;
$R^7$ is absent when m is 0 and is (—H, —H), =O, (—H, —F) or (—H, —OCH$_3$) when m is 1; or
$R^6$ and $R^7$, where both are present, together with the bonds with which they are attached, form a carbocyclic or heterocyclic ring system such that a bicyclic nitrogen-containing heterocyclic system is formed;
Q is $C_1$-$C_6$ alkyl, —CH$_2$CF$_3$, —C(O)CH$_2$CH$_3$, —C(O)CH$_2$CH$_2$CH$_3$, —C(O)CH(CH$_3$)$_2$, —OCH$_3$, —CH$_2$OCH$_3$ or —CO$_2$CH$_2$CH$_3$, or Q is represented by the formula:

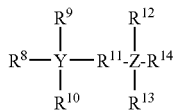

wherein: $R^8$ is a bond, —CH$_2$—, —CH$_2$CH$_2$—, or —CO$_2$CH$_2$CH$_2$—;
Y is a bond, H, $C_3$-$C_7$ cycloalkyl, phenyl, 5-7 membered heterocyclyl or 5-6 membered heteroaryl;
$R^9$ is not present, or $R^9$ is H, F, Cl, =O, =N, —C≡N, —CH$_2$C≡N, —CH$_2$CH$_2$C≡N or $C_1$-$C_6$ alkyl;
$R^{10}$ is not present, or $R^{10}$ is H, F, Cl, Br, —NH$_2$, —CH$_3$, —CH$_2$CH$_3$, —CF$_3$, —OH, —OCH$_3$, —OCH(CH$_3$)$_2$, —CH$_2$OCH$_3$, —C(O)NH$_2$, =O, —CO$_2$CH$_2$CH$_3$, —NHCH$_2$CH$_2$OH, —NHCO$_2$CH$_3$, —NHCO$_2$CH$_2$CH$_3$, —NHCO$_2$C(CH$_3$)$_2$CH$_3$, —N(CH$_3$)$_2$, or heteroaryl optionally substituted with methyl;
$R^{11}$ is not present or $R^{11}$ is a bond, H, —CH$_2$—, —NH—, —CH$_2$CH$_2$—, —OCH$_2$—, —CO—, —CO$_2$CH$_2$CH$_2$—, —C(O)NH—, —C(O)NHCH$_2$—, —C(O)NHCH$_2$CH$_2$—, —NHCO$_2$—, —NHCO$_2$CH$_2$—, —NHCO$_2$CH$_2$CH$_2$— or —NHCO$_2$C(CH$_3$)$_2$CH$_2$—;
Z is not present, or Z is a bond, H, $C_1$-$C_3$ alkyl, $C_3$-$C_7$ cycloalkyl, phenyl, 5-7 membered heterocyclyl or 5-6 membered heteroaryl;
$R^{12}$ is not present, or $R^{12}$ is H, F, Cl, —CH$_3$, —CH$_2$CH$_3$, —OCH$_3$, —CO$_2$CH$_2$CH$_3$, —NHCO$_2$CH$_3$, —NHCO$_2$CH$_2$CH$_3$ or —NHCO$_2$C(CH$_3$)$_2$CH$_3$;
$R^{13}$ is not present, or $R^{13}$ is H, F, Cl, —CH$_3$, —CH$_2$CH$_3$, —OCH$_3$, —CO$_2$CH$_2$CH$_3$, —NHCO$_2$CH$_3$, —NHCO$_2$CH$_2$CH$_3$ or NHCO$_2$C(CH$_3$)$_2$CH$_3$;
$R^{14}$ is not present, or $R^{14}$ is H, =O, —OH, $C_1$-$C_6$ alkyl, —CH$_3$, —CF$_3$, —OCH$_3$, —OCH$_2$CH$_3$, —OCH(CH$_3$)$_2$, —O(CH$_2$)$_2$OH, —CO$_2$CH$_2$CH$_3$, F, Cl, Br, =N, —C≡N, —N(CH$_3$)$_2$, —C(O)CH$_3$, —C(O)NH$_2$, —CH$_2$CH$_2$OH, —C(O)NHCH$_3$, —C(O)N(CH$_2$CH$_3$)$_2$, sulfonyl, ($C_1$-$C_3$)alkylsulfonyl, aminosulfonyl, ($C_1$-$C_3$) alkylaminosulfonyl, 2-methylbutanolyl, 1-methoxy-2-methylbutanyl, 2-methylhex-5-ene-2-yl, —N(CH$_3$)$_2$, N-ethyl-N-methylethanaminyl, 5-6 membered cycloalkyl, 5-7 membered heterocyclyl, 5-6 membered heteroaryl or phenyl, wherein each cyclic system is optionally substituted with H, —CH$_3$, or —C≡N, and wherein when $R^{14}$ is cycloalkyl, heterocyclyl, phenyl or heteroaryl, and when Z is a cycloalkyl, heterocyclyl, phenyl or heteroaryl, $R^{14}$ and Z may form a bicyclic ring system,
and wherein when Y is a cyclic system and $R^{11}$ and is not present, Y and Z may form a saturated, partially unsaturated or aromatic bicyclic carbocyclic or heterocyclic ring system or a saturated, partially unsaturated or aromatic spiro-fused carbocyclic or heterocyclic ring system.

Referring to a compound of formula (I), Q is preferably $C_1$-$C_6$ alkyl, —CH$_2$CF$_3$, —C(O)CH$_2$CH$_3$, —C(O)CH$_2$CH$_2$CH$_3$, —C(O)CH(CH$_3$)$_2$, —OCH$_3$, —CH$_2$OCH$_3$, —CO$_2$CH$_2$CH$_3$, —(CH$_2$)$_n$-D, —(CH$_2$)$_n$-D-E, —(CH$_2$)$_n$-D-E-F or —(CH$_2$)$_n$—CO-D, wherein:

D is (a) phenyl; (b) naphthyl; (c) a five-membered aromatic heterocyclic group containing either (i) 1-4 nitrogen atoms or (ii) 0-3 nitrogen atoms and 1 oxygen or 1 sulphur atom; (d) a six-membered aromatic heterocyclic group containing 1-3 nitrogen atoms; (e) a nine-membered bicyclic aromatic heterocyclic group containing either (i) 1-5 nitrogen atoms or (ii) 0-4 nitrogen atoms and 1 oxygen or 1 sulphur atom; (f) a ten-membered bicyclic aromatic or partially saturated heterocyclic group containing 1-6 nitrogen atoms; (g) a five- or six-membered saturated or partially unsaturated heterocyclic group containing one or two nitrogen or oxygen groups; (h) a $C_3$-$C_6$ cycloalkyl or cycloalkenyl group, optionally benzo-fused; each of said groups (a)-(h) being optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —(CH$_2$)$_p$OH, —(CH$_2$)$_p$CN, halo, oxo, —(CH$_2$)$_p$NR$^{18}$R$^{19}$, —(CH$_2$)$_p$CONR$^{18}$R$^{19}$, —(CH$_2$)$_p$OR$^{18}$, —(CH$_2$)$_p$COR$^{18}$ and —(CH$_2$)$_p$COOR$^{18}$, wherein p is 0-3 and $R^{18}$ and $R^{19}$ are each H or $C_1$-$C_6$ alkyl optionally substituted with —OH or $C_1$-$C_6$ alkoxy;

n is 0 or 1;

E is $C_1$-$C_6$ alkylene or $C_1$-$C_6$ cycloalkylene, wherein one or two —CH$_2$— groups of said $C_1$-$C_6$ alkylene or $C_1$-$C_6$ cycloalkylene may each be replaced with a group independently selected from —NH—, —CO— and —O—;

F is (a) phenyl; (b) naphthyl; (c) a five-membered aromatic heterocyclic group containing either (i) 1-4 nitrogen atoms or (ii) 0-3 nitrogen atoms and 1 oxygen or 1 sulphur atom; (d) a six-membered aromatic heterocyclic group containing 1-3 nitrogen atoms; (e) a nine-membered bicyclic aromatic heterocyclic group containing either (i) 1-5 nitrogen atoms or (ii) 0-4 nitrogen atoms and 1 oxygen or 1 sulphur atom; (f) a ten-membered bicyclic aromatic heterocyclic group containing 1-6 nitrogen atoms; (g) a five- or six-membered saturated or partially unsaturated heterocyclic group containing one or two nitrogen or oxygen groups; (h) a $C_3$-$C_6$ cycloalkyl or cycloalkenyl group, optionally benzo-fused; each of said groups (a)-(h) being optionally substituted by one or more of $C_1$-$C_6$ alkyl, $C_1$-$C_6$ fluoroalkyl, $C_3$-$C_6$ cycloalkyl, hydroxy ($C_3$-$C_6$ cycloalkyl), $C_1$-$C_6$ alkenyl, —(CH$_2$)$_p$OH, —(CH$_2$)$_p$CN, halo, —(CH$_2$)$_p$NR$^{18}$R$^{19}$, —(CH$_2$)$_p$CONR$^{18}$R$^{19}$, —(CH$_2$)$_p$OR$^8$, —(CH$_2$)$_p$COR$^{18}$ and —(CH$_2$)$_p$COOR$^{18}$, wherein p is 0-3 and $R^{18}$ and $R^{19}$ are each H or $C_1$-$C_6$ alkyl optionally substituted with —OH or $C_1$-$C_6$ alkoxy;

Compounds in which Q is —(CH$_2$)$_n$-D, optionally substituted as described above, are particularly preferred, especially when n is 0, most especially when n is 0 and D is a ten-membered bicyclic aromatic or partially saturated heterocyclic group containing 1-6 nitrogen atoms, optionally substituted as described above. For example, Q may be an optionally substituted 5,6,7,8-tetrahydropyrido[4,3-d]pyrimidin-2-yl group, such as 6-methyl-5,6,7,8-tetrahydropyrido[4,3-d]pyrimidin-2-yl. More specifically Q may be methyltetrazolyl such as 1-methyltetrazol-5-yl.

Suitable choices for Q include isopropyl, (trifluoromethyl)methyl, 1-oxo-butan-1-yl, ethoxycarbonyl and the following (Me=methyl, Et=ethyl):

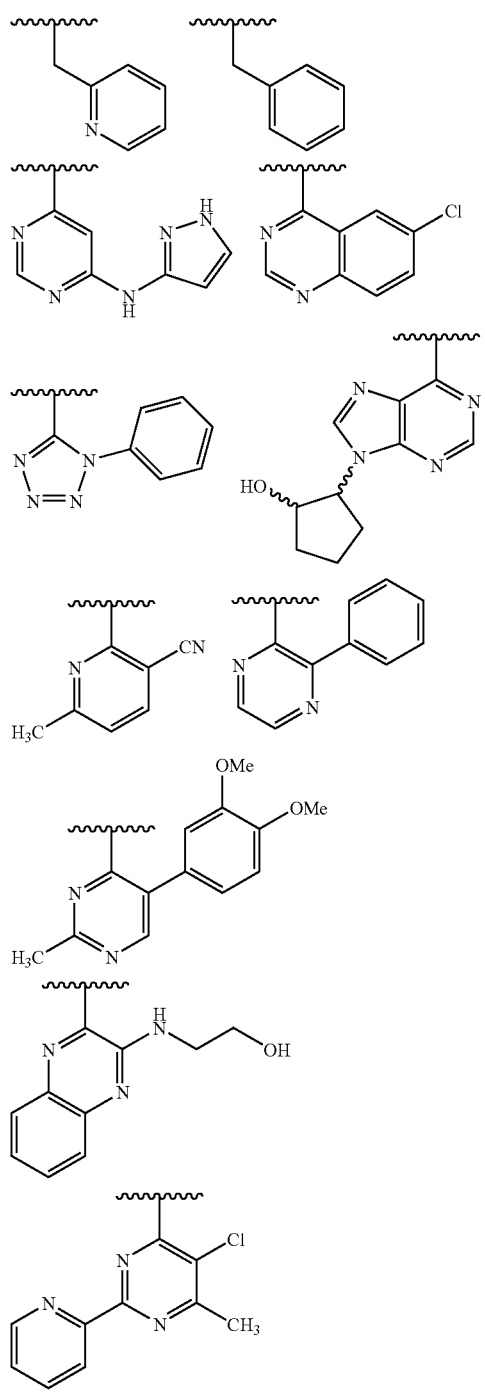

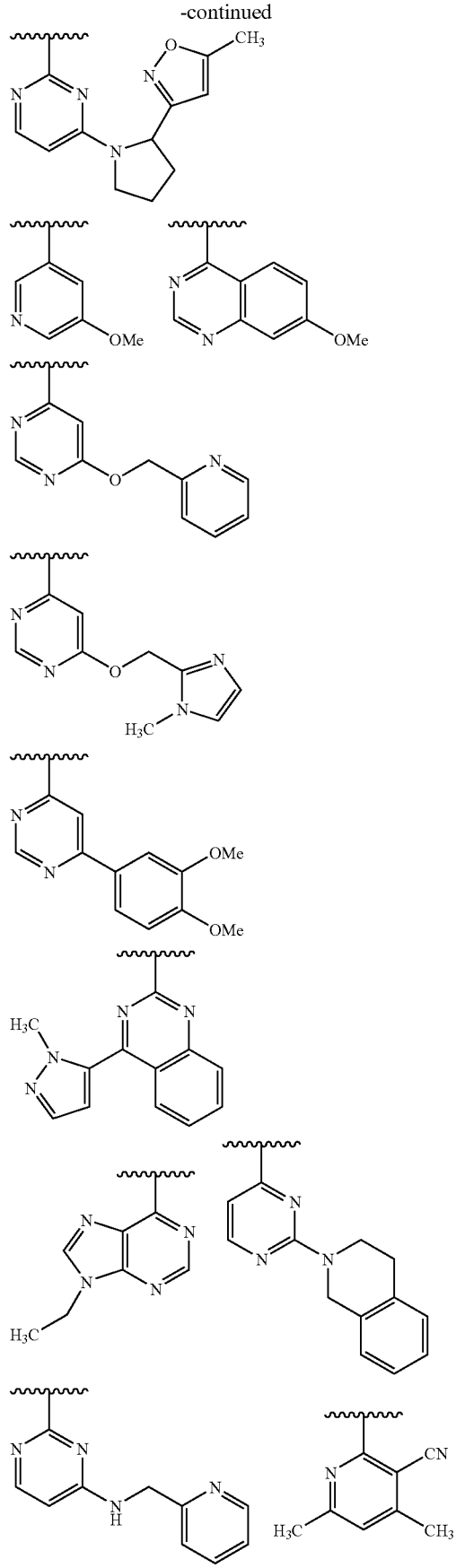

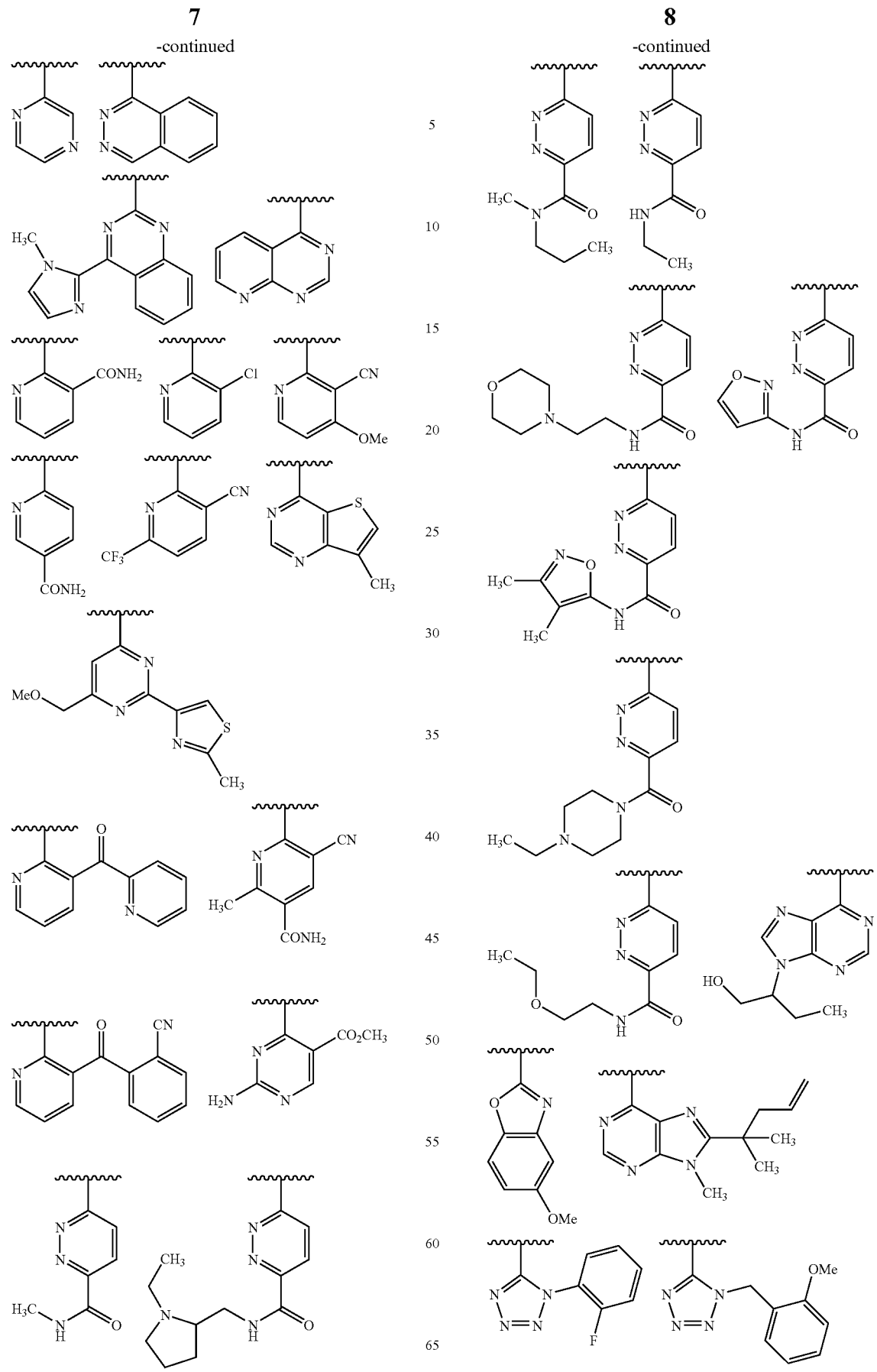

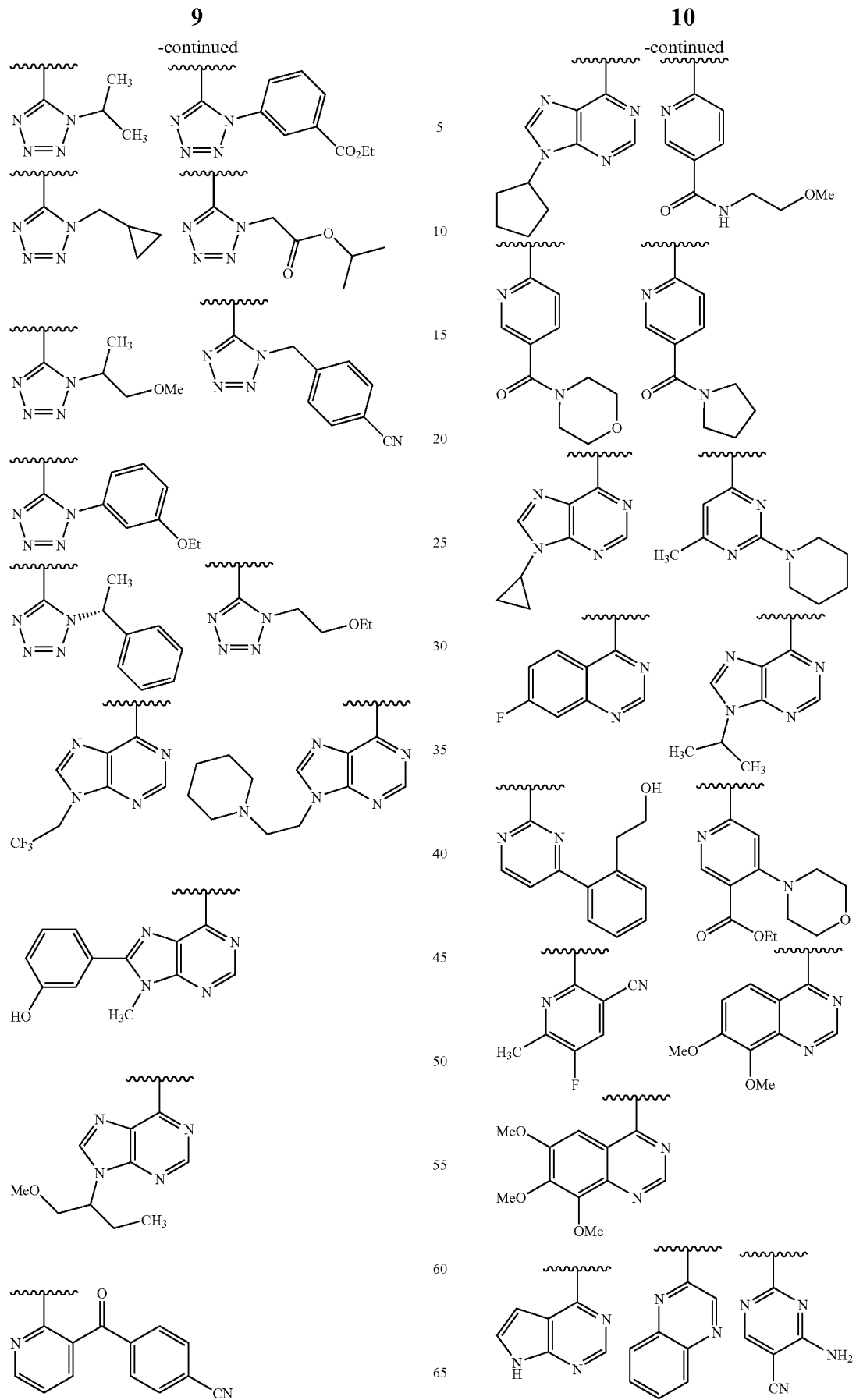

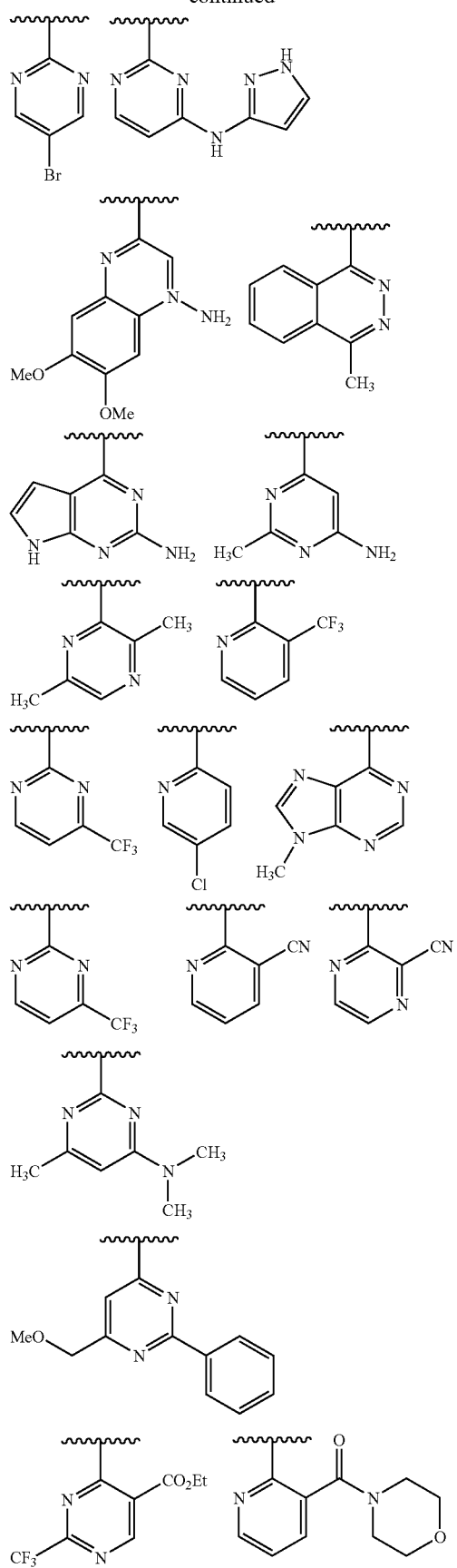
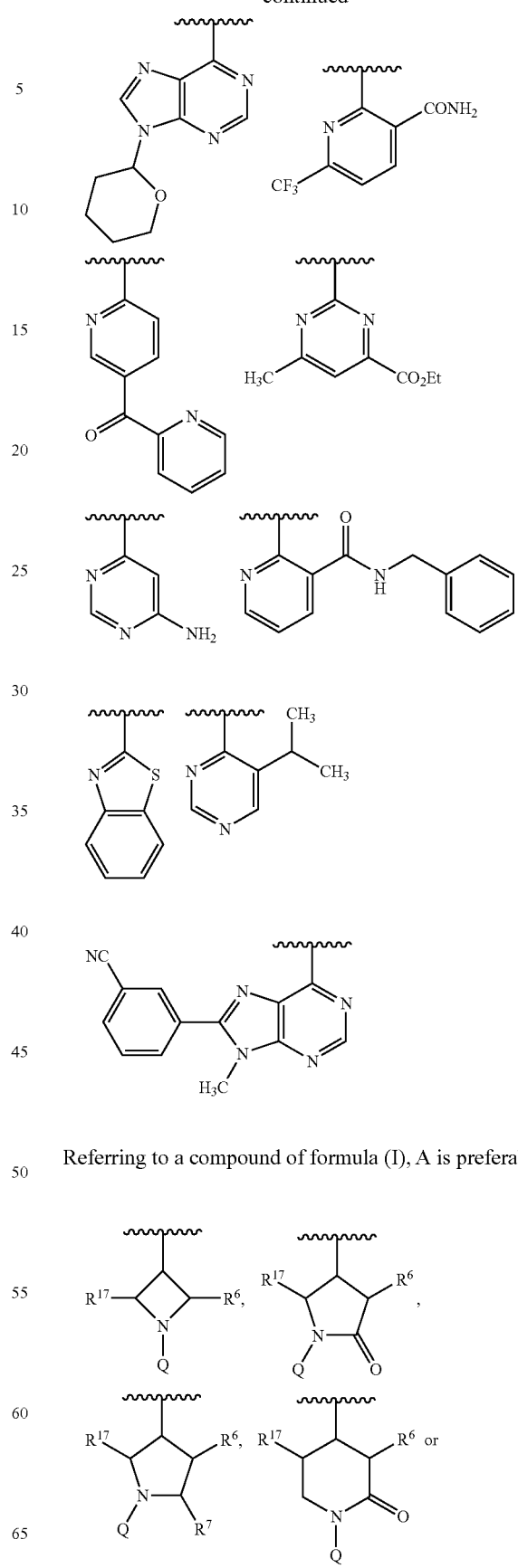
Referring to a compound of formula (I), A is preferably:
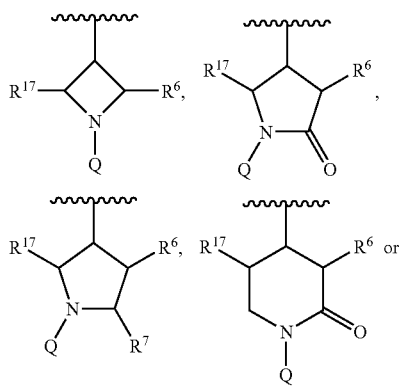

-continued

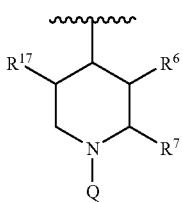

wherein R[6] is H or OH and R[17] is H, or R[6] and R[17] form a zero, one or two carbon bridge across the ring; and R[7] is H, F or —OCH₃; or R[6] and R[7], where both are present, together with the bonds with which they are attached, form a carbocyclic or heterocyclic ring system such that a bicyclic nitrogen-containing heterocyclic system is formed.

Most preferably, A is:

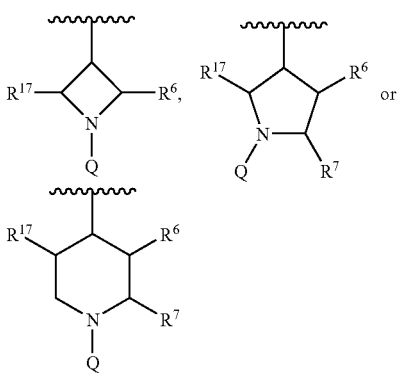

wherein: R[6] is H and R[17] is H, or R[6] and R[17] form a zero, one or two carbon bridge across the ring; and R[7] is H, F or —OCH₃.

In one most preferred embodiment, A is 3-pyrrolidinyl substituted at the 1-position by Q.

In one embodiment, the invention provides a compound of formula (I), or a pharmaceutically acceptable salt or solvate thereof, in which Q is represented by the formula:

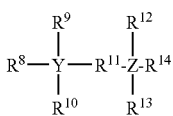

wherein R[8], R[9], R[10], R[11], R[12], R[13], R[14], Y and Z are as defined above.

In another embodiment, the invention provides a compound of Formula (I), or a pharmaceutically acceptable salt or solvate thereof, in which A, L, R[2], R[5] and R[15] are as defined above and R[1], R[3] and R[4] are independently H, F, Cl, CHF₂, CF₃, or OH. In a preferred aspect of this embodiment, Q is represented by the formula:

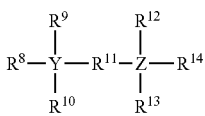

wherein R[8], R[9], R[10], R[11], R[12], R[13], R[14], Y and Z are as defined above.

In another embodiment, the invention provides a compound of Formula (II):

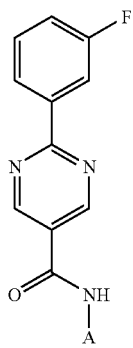

(II)

or a pharmaceutically acceptable salt or solvate thereof, wherein A is as defined above for a compound of formula (I).

In another embodiment, the invention provides a compound of Formula (III):

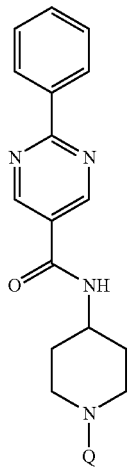

(III)

or a pharmaceutically acceptable salt or solvate thereof, wherein Q is as defined above for a compound of formula (I).

In another embodiment, the invention provides a compound of Formula (IV):

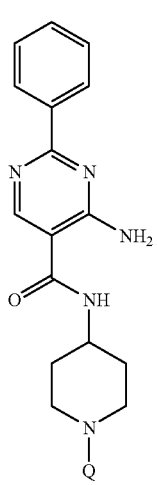

(IV)

or a pharmaceutically acceptable salt or solvate thereof, wherein Q is as defined above for a compound of formula (I).

In another embodiment, the invention provides a compound of Formula (V):

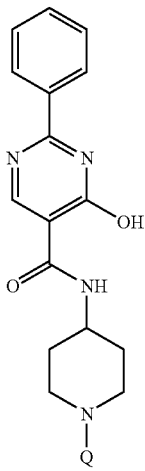

(V)

or a pharmaceutically acceptable salt or solvate thereof, wherein Q is as defined above for a compound of formula (I).

In another embodiment, the invention provides a compound of Formula (VI):

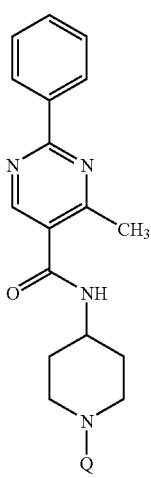

(VI)

or a pharmaceutically acceptable salt or solvate thereof, wherein Q is as defined above for a compound of formula (I).

In another embodiment, the invention provides a compound of Formula (VII):

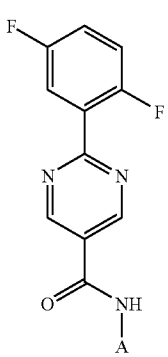

(VII)

or a pharmaceutically acceptable salt or solvate thereof, wherein A is as defined above for a compound of formula (I).

In another embodiment, the invention provides a compound of Formula (VIII):

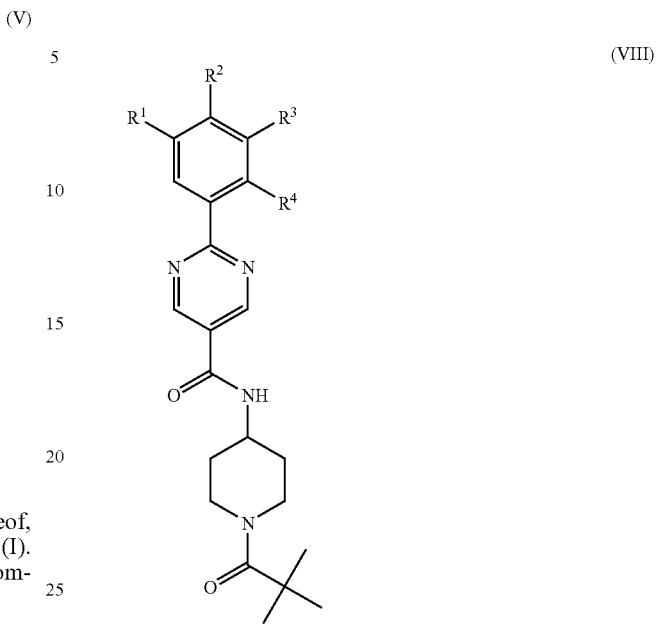

(VIII)

or a pharmaceutically acceptable salt or solvate thereof, wherein $R^1$, $R^2$, $R^3$ and $R^4$ are as defined above for a compound of formula (I).

In another embodiment, the invention provides a compound of Formula (IX):

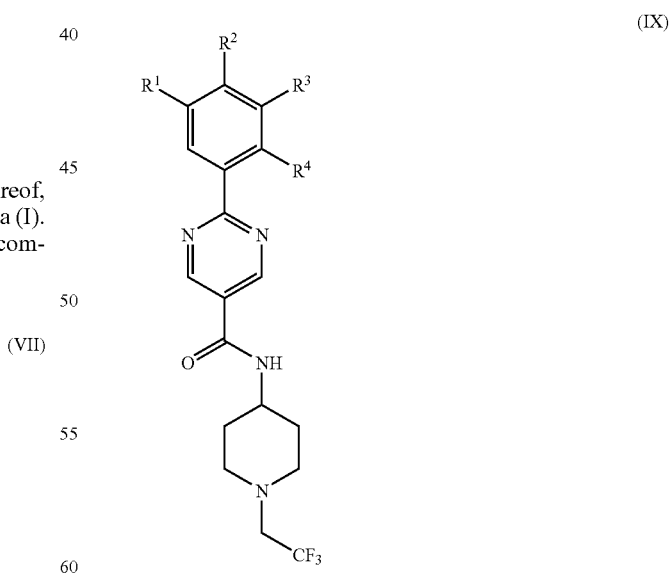

(IX)

or a pharmaceutically acceptable salt or solvate thereof, wherein $R^1$, $R^2$, $R^3$ and $R^4$ are as defined above for a compound of formula (I).

In another embodiment, the invention provides a compound of Formula (X):

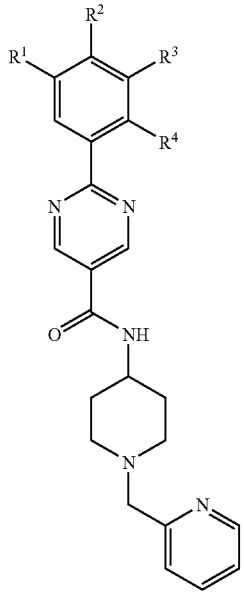

(X)

or a pharmaceutically acceptable salt or solvate thereof, wherein $R^1$, $R^2$, $R^3$ and $R^4$ are as defined above for a compound of formula (I).

In another embodiment, the invention provides a compound of Formula (Ia):

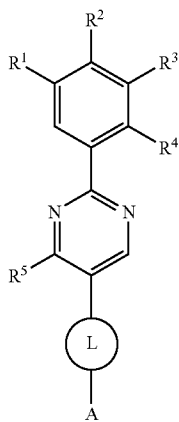

(Ia)

or a pharmaceutically acceptable salt or solvate thereof, wherein:

$R^1$, $R^3$ and $R^4$ are independently H, F, Cl, —CHF$_2$, —CF$_3$, —OH, —CH$_2$OH, —CH$_2$CH$_2$OH, —C≡N, —CH$_2$C≡N, —CH$_2$CH$_2$C≡N, C$_1$-C$_5$ alkyl, C(O)OR$^{16}$, —NC(O)R$^{16}$, —NS(O)$_2$R$^{16}$, —C(O)R$^{16}$, or —OCH$_3$;

$R^{16}$ is C$_1$-C$_5$ alkyl;

$R^2$ is H or F;

$R^5$ is H, —NH$_2$, —OH or —CH$_3$;

L is —C(O)NH—, —NHC(O)— or —CH$_2$NHC(O)—; and

A is selected from the group consisting of:

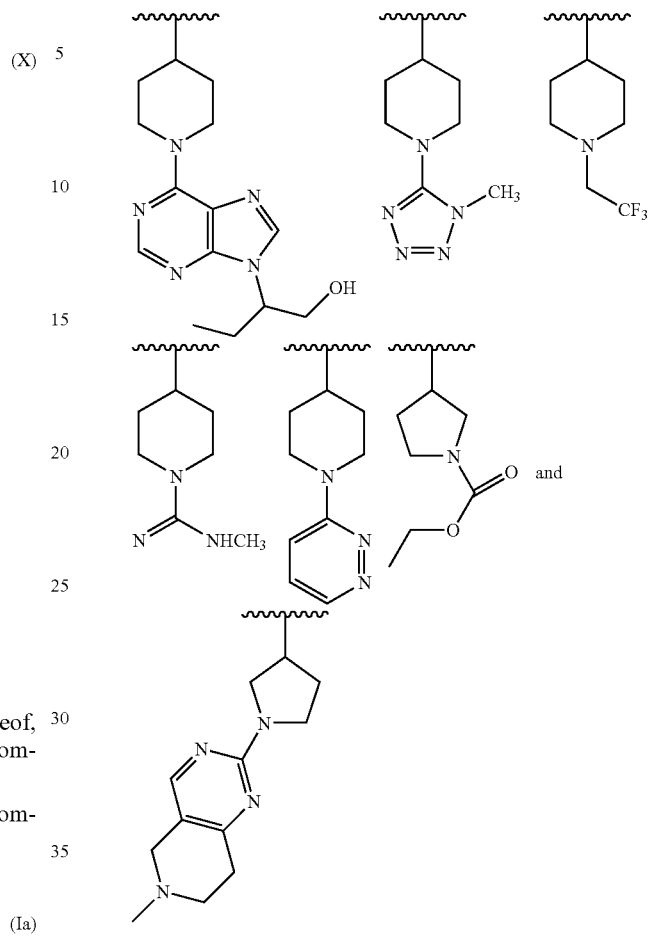

In another embodiment, the invention provides a compound selected from the group consisting of:

ethyl 3-(2-(3-fluorophenyl)pyrimidine-5-carboxamido)pyrrolidine-1-carboxylate;

N-(1-(7,8-dihydro-5H-pyrano[4,3-d]pyrimidin-2-yl)pyrrolidin-3-yl)-2-(3-fluorophenyl)pyrimidine-5-carboxamide;

2-(3-fluorophenyl)-N-{1-[(methylamino)carbonyl]piperidin-4-yl}pyrimidine-5-carboxamide;

2-(3-fluorophenyl)-N-[1-(6-methyl-5,6,7,8-tetrahydropyrido[4,3-d]pyrimidin-2-yl)pyrrolidin-3-yl]pyrimidine-5-carboxamide; and 2-(3-fluorophenyl)-N-[1-(2,2,2-trifluoroethyl)piperidin-4-yl]pyrimidine-5-carboxamide. and the pharmaceutically acceptable salts and solvates thereof.

A preferred specific compound is 2-(3-fluorophenyl)-N-[1-(6-methyl-5,6,7,8-tetrahydropyrido[4,3-d]pyrimidin-2-yl)pyrrolidin-3-yl]pyrimidine-5-carboxamide, particularly in the form of the stereoisomer 2-(3-fluorophenyl)-N-[(3S)-1-(6-methyl-5,6,7,8-tetrahydropyrido[4,3-d]pyrimidin-2-yl)pyrrolidin-3-yl]pyrimidine-5-carboxamide.

The present invention also provides: a method of treating a disease or condition mediated at least in part by prostaglandin D$_2$ produced by H-PGDS, in a subject in need of such treatment, comprising administering to the subject a therapeutically effective amount of a compound of formula (I), or a pharmaceutically acceptable salt or solvate thereof; the use of a compound of formula (I), or a pharmaceutically acceptable salt or solvate thereof, for the manufacture of a medicament for treating a disease or condition mediated at least in part by prostaglandin D$_2$ produced by H-PGDS; a compound of formula (I), or a pharmaceutically acceptable salt or solvate thereof, for use as a medicament; a compound of formula (I), or a pharmaceutically acceptable salt or solvate thereof, for use in the treatment of a disease or condition mediated at least in part by prostaglandin $D_2$ produced by H-PGDS; a pharmaceutical composition comprising a compound of formula (I), or a pharmaceutically acceptable salt or solvate thereof, and a pharmaceutically acceptable excipient; a pharmaceutical composition for the treatment of a disease or condition mediated at least in part by prostaglandin $D_2$ produced by H-PGDS comprising a compound of formula (I), or a pharmaceutically acceptable salt or solvate thereof.

The diseases and conditions mediated at least in part by prostaglandin $D_2$ produced by H-PGDS include allergy and allergic inflammation. Important diseases and conditions of this kind are allergic respiratory conditions such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, airways disease that is associated with pulmonary hypertension, acute lung injury, bronchiectasis, sinusitis, allergic conjunctivitis or atopic dermatitis, particularly asthma or chronic obstructive pulmonary disease.

Types of asthma include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

Included in the use of the compounds of formula (I) for the treatment of asthma, is palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

Other important diseases and conditions mediated at least in part by prostaglandin $D_2$ produced by H-PGDS are arthritis (especially rheumatoid arthritis), irritable bowel diseases (such as Crohns disease and ulcerative colitis), irritable bowel syndrome, chronic pain, skin inflammation and irritation (such as eczema), niacin-induced skin flushing and cealic type disease (e.g. as a result of lactose intolerance). Chronic pain conditions include neuropathic pain conditions (such as painful diabetic neuropathy and postherpetic neuralgia), carpal tunnel syndrome, back pain, headache, cancer pain, arthritic pain and chronic post-surgical pain.

The present invention also provides any of the uses, methods or compositions as defined above wherein the compound of formula (I), or pharmaceutically acceptable salt or solvate thereof, is used in combination with another pharmacologically active compound, particularly one of the compounds listed in Table 1 below. Specific combinations useful according to the present invention include combinations comprising a compound of formula (I), or a pharmaceutically acceptable salt or solvate thereof, and (i) a glucocorticosteroid or DAGR (dissociated agonist of the corticoid receptor); (ii) a $\beta_2$ agonist, an example of which is a long-acting $\beta_2$ agonist; (iii) a muscarinic M3 receptor antagonist or an anticholinergic agent; (iv) a histamine receptor antagonist, which may be an H1 or an H3 antagonist; (v) a 5-lypoxygenase inhibitor; (vi) a thromboxane inhibitor; or (vii) an $LTD_4$ inhibitor. Generally, the compounds of the combination will be administered together as a formulation in association with one or more pharmaceutically acceptable excipients.

TABLE I (a) 5-Lipoxygenase activating protein (FLAP) antagonists
(b) Leukotriene antagonists (LTRAs) including antagonists of $LTB_4$, $LTC_4$, $LTD_4$, and $LTE_4$
(c) Histamine receptor antagonists including H1 and H3 antagonists
(d) $\alpha_1$- and $\alpha_2$-Adrenoceptor agonist vasoconstrictor sympathomimetic agents for decongestant use
(e) Muscarinic M3 receptor antagonists or anticholinergic agents
(f) PDE inhibitors, e.g. PDE3, PDE4 and PDE5 inhibitors, such as theophylline
(g) Sodium cromoglycate
(h) COX inhibitors, including both non-selective and selective COX-1 or COX-2 inhibitors (such as NSAIDs)
(i) Glucocorticosteroids or DAGR (dissociated agonists of the corticoid receptor)
(j) Monoclonal antibodies active against endogenous inflammatory entities
(k) β2 agonists, including long-acting β2 agonists
(l) Integrin antagonists
(m) Adhesion molecule inhibitors, including VLA-4 antagonists
(n) Kinin-$B_1$- and $B_2$-receptor antagonists
(o) Immunosuppressive agents, including inhibitors of the IgE pathway, and cyclosporin;
(p) Inhibitors of matrix metalloproteases (MMPs), such as., MMP9, and MMP12
(q) Tachykinin $NK_1$, $NK_2$ and $NK_3$ receptor antagonists
(r) Protease inhibitors, such as elastase inhibitors, chymase and cathepsin G;
(s) Adenosine A2a receptor agonists and A2b antagonists
(t) Inhibitors of urokinase
(u) Compounds that act on dopamine receptors, such as D2 agonists
(v) Modulators of the NFκB pathway, such as IKK inhibitors
(w) Modulators of cytokine signaling pathways such as syk kinase, JAK kinase inhibitors, p38 kinase, SPHK-1 kinase, Rho kinase, EGF-R or MK-2
(x) Agents that can be classed as mucolytics or anti-tussive, and mucokinetics;
(y) Antibiotics;
(z) Antivirals;
(aa) Vaccines
(bb) Chemokines TABLE I-continued (cc) Epithelial sodium channel (ENaC) blockers or Epithelial sodium channel (ENaC) inhibitors
(dd) P2Y2 Agonists and other Nucleotide receptor agonists
(ee) Inhibitors of thromboxane
(ff) Niacin
(gg) Inhibitors of 5-lypoxygenase (5-LO)
(hh) Adhesion factors including VLAM, ICAM, and ELAM Besides being useful for human treatment, compounds of formula (I) are also useful for veterinary treatment of companion animals, exotic animals and farm animals.

When used in the present application, the following abbreviations have the meanings set out below:
HATU is N,N, N',N'-tetramethyl-O-(7-azabenzotriazol-1-yl) uronium hexafluorophosphate;
HOBt is 1-hydroxybenzotriazole;
BOP is (benzotriazol-1-yloxy)tris(dimethylamino)phosphonium hexafluorophosphate;
HBTU is N,N,N',N'-tetramethyl-O-(1H-benzotriazol-1-yl) uronium hexafluorophosphate;
TBTU is O-(benzotriazol-1-yl)-N,N, N',N'-tetramethyluronium tetrafluoroborate;
DIPEA is N,N-diisopropylethylamine;
TEA is triethylamine;
TFA is trifluoroacetic acid;
DCM is dichloromethane;
DMA is N,N-dimethylacetamide;
EDC/EDAC is N-(3-Dimethylaminopropyl)-N'-ethylcarbodiimide hydrochloride;
NMM is 4-methylmorpholine;
DCC is N,N'-dicyclohexylcarbodiimide;
HOAt is 1-hydroxy-7-azabenzotriazole;
Me is methyl;
Et is ethyl;
iPr is isopropyl; and
$CO_2Et$ is ethyl carboxylate.

Unless otherwise defined herein, scientific and technical terms used in connection with the present invention shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, a reduction in relapses, improvement in quality of life and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

The term "alkyl", alone or in combination, means an acyclic alkyl radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like. Where no specific substitution is specified, alkyl radicals can be optionally substituted with groups consisting of hydroxy, methoxy, amino, cyano, chloro, and fluoro. Examples of such substituted alkyl radicals include chloroethyl, hydroxyethyl, cyanobutyl, aminopentyl and the like.

The carbon atom content of various hydrocarbon-containing moieties is indicated by a prefix designating a lower and upper number of carbon atoms in the moiety, that is, the prefix $C_{i-j}$ indicates a moiety of the integer "i" to the integer "j" carbon atoms, inclusive. Thus, for example, '$C_{1-6}$ alkyl' or '$C_1$-$C_6$ alkyl' refers to alkyl of one to six carbon atoms, inclusive.

The term "hydroxyl," as used herein, means an OH radical.

The terms 'heterocycle', 'heterocylic ring system' and 'heterocyclyl' refer to a saturated or unsaturated mono- or multi-ring cycloalkyl wherein one or more carbon atoms is replaced by N, S or O. This includes, for example, the following structures:

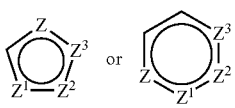

wherein Z, $Z^1$, $Z^2$ and $Z^3$ are C, S, O, or N, with the proviso that one of Z, $Z^1$, $Z^2$ or $Z^3$ is other than carbon, but is not O or S when attached to another Z atom by a double bond or when attached to another O or S atom. Wherein Z, $Z^1$, $Z^2$ or $Z^3$ is S or N, the atom may be substituted by oxygen to form a sulfinyl (S=O), sulfonyl (S(=O)$_2$), or N-oxide ($N^+$—$O^-$) radical. The term "heterocycle" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocycle" or also includes partially unsaturated ring structures such as dihydrofuranyl, pyrazolinyl, imidazolinyl, pyrrolinyl, chromanyl, dihydrothiophenyl, and others.

The term 'heteroaryl' refers to an aromatic heterocyclic group. Heteroaryl is preferably: (a) a five-membered aromatic heterocyclic group containing either (i) 1-4 nitrogen atoms or (ii) 0-3 nitrogen atoms and 1 oxygen or 1 sulphur atom; (b) a six-membered aromatic heterocyclic group containing 1-3 nitrogen atoms; (c) a nine-membered bicyclic aromatic heterocyclic group containing either (i) 1-5 nitrogen atoms or (ii) 0-4 nitrogen atoms and 1 oxygen or 1 sulphur atom; or (d) a ten-membered bicyclic aromatic heterocyclic group containing 1-6 nitrogen atoms; each of said groups (a)-(d) being optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —$(CH_2)_p$OH, —$(CH_2)_p$CN, halo, oxo, —$(CH_2)_p NR^{18}R^{19}$, —$(CH_2)_p CONR^{18}R^{19}$, —$(CH_2)_p OR^{18}$, —$(CH_2)_p COR^{18}$ and —$(CH_2)_p COOR^{18}$, wherein p is 0-3 and $R^{18}$ and $R^{19}$ are each H or $C_1$-$C_6$ alkyl optionally substituted with —OH or $C_1$-$C_6$ alkoxy. Examples of "heteroaryl" include pyridyl, pyrimidinyl, pyridazinyl, pyrazinyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl (optionally substituted as specified above).

A preferred non-aromatic heterocyclic group is a five- or six-membered saturated or partially unsaturated heterocyclic group containing one or two nitrogen or oxygen groups, optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —$(CH_2)_p$OH, —$(CH_2)_p$CN, halo, oxo, —$(CH_2)_p NR^{18}R^{19}$, —$(CH_2)_p CONR^{18}R^{19}$, —$(CH_2)_p OR^{18}$, —$(CH_2)_p COR^{18}$ and —$(CH_2)_p COOR^{18}$, wherein p is 0-3 and $R^{18}$ and $R^{19}$ are each H or $C_1$-$C_6$ alkyl optionally substituted with —OH or $C_1$-$C_6$ alkoxy. Preferred examples of non-aromatic heterocyclic groups include azetidinyl, pyrrolidinyl, tetrahydrofuranyl, piperidininyl, piperazinyl and morpholinyl (optionally substituted as specified above).

In either "heterocyle" or "heteroaryl," the point of attachment to the molecule of interest can be at the heteroatom or elsewhere within the ring.

The term "nitrogen-containing heterocycle," or "nitrogen containing heteroaryl," as used herein to describe the present invention, means a heterocyclic or heteroaryl group, respectively, that comprises at least one nitrogen atom. Such substitutents may also be referred to herein as "heterocycle containing at least one nitrogen," and "heteroaryl containing at least one nitrogen."

The term "cycloalkyl" or "carbocyclyl" means a mono- or multi-ringed cycloalkyl wherein each ring contains three to seven carbon atoms, preferably three to six carbon atoms. 'Cycloalkyl' is preferably a monocyclic cycloalkyl containing from three to seven carbon atoms. Examples include cyclopropyl, cyclobutyl, cyclopentyl, cyclohexyl, and cycloheptyl.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring cycloalkyl having a cyclic array of p-orbitals containing 4n+2 electrons, including, but not limited to, substituted or unsubstituted phenyl, naphthyl, or anthracenyl optionally fused to a carbocyclic radical wherein aryl is optionally substituted with one or more substituents selected from the group consisting of: (a) halo; (b) $C_{1-6}$alkoxy optionally substituted by halo and phenyl; (c) $C_{1-6}$alkyl optionally substituted by halo; (d) phenyl; (e) O-phenyl; (f) cyano; (g) nitro; (h) hydroxyl, or any two adjacent substituents taken together constitute a group of the formula —$O(CH_2)_mO$— where m is 1-3.

The symbols

and

denote the point of attachment of a substituent.

As used herein, the terms "co-administration", "co-administered" and "in combination with", referring to a combination of a compound of formula (I) and one or more other therapeutic agents, is intended to mean, and does refer to and include the following:

simultaneous administration of such a combination of a compound of formula (I) and a further therapeutic agent to a patient in need of treatment, when such components are formulated together into a single dosage form which releases said components at substantially the same time to said patient, substantially simultaneous administration of such a combination of a compound of formula (I) and a further therapeutic agent to a patient in need of treatment, when such components are formulated apart from each other into separate dosage forms which are taken at substantially the same time by said patient, whereupon said components are released at substantially the same time to said patient, sequential administration of such a combination of a compound of formula (I) and a further therapeutic agent to a patient in need of treatment, when such components are formulated apart from each other into separate dosage forms which are taken at consecutive times by said patient with a significant time interval between each administration, whereupon said components are released at substantially different times to said patient; and sequential administration of such a combination of a compound of formula (I) and a further therapeutic agent to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

The term 'excipient' is used herein to describe any ingredient other than a compound of formula (I). The choice of excipient will to a large extent depend on factors such as the particular mode of administration, the effect of the excipient on solubility and stability, and the nature of the dosage form. The term "excipient" encompasses diluent, carrier or adjuvant.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphatlene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) may also exist in unsolvated and solvated forms. The term 'solvate' is used herein to describe a molecular complex comprising the compound of formula (I), or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (Aug. 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) (also referred to as compounds of the invention) include references to salts, solvates, multi-component complexes and liquid crystals thereof and to solvates, multi-component complexes and liquid crystals of salts thereof.

Also included within the scope of the invention are all polymorphs and crystal habits of compounds of formula (I), prodrugs and isomers thereof (including optical, geometric and tautomeric isomers) as hereinafter defined and isotopically-labeled forms thereof.

As indicated, so-called 'prodrugs' of the compounds of formula (I) are also within the scope of the invention. Thus certain derivatives of a compound of formula (I) which may have little or no pharmacological activity themselves can, when administered into or onto the body, be converted into a compound of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include:
(i) where the compound of formula (I) contains a carboxylic acid functionality (—COOH), an ester thereof, for example, a compound wherein the hydrogen of the carboxylic acid functionality of the compound of formula (I) is replaced by ($C_1$-$C_8$)alkyl;
(ii) where the compound of formula (I) contains an alcohol functionality (—OH), an ether thereof, for example, a compound wherein the hydrogen of the alcohol functionality of the compound of formula (I) is replaced by ($C_1$-$C_6$)alkanoyloxymethyl; and
(iii) where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by ($C_1$-$C_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include
(i) where the compound of formula (I) contains a methyl group, an hydroxymethyl derivative thereof (—$CH_3$->—$CH_2OH$):
(ii) where the compound of formula (I) contains an alkoxy group, an hydroxy derivative thereof (—OR->—OH);
(iii) where the compound of formula (I) contains a tertiary amino group, a secondary amino derivative thereof (—$NR^1R^2$->—$NHR^1$ or —$NHR^2$);
(iv) where the compound of formula (I) contains a secondary amino group, a primary derivative thereof (—$NHR^1$->—$NH_2$);
(v) where the compound of formula (I) contains a phenyl moiety, a phenol derivative thereof (-Ph->-PhOH); and
(vi) where the compound of formula (I) contains an amide group, a carboxylic acid derivative thereof (—$CONH_2$->COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or 1-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of formula (I) (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art. (See, for example, Smith, Roger M. Loughborough University, Loughborough, UK. Chromatographic Science Series (1998), 75 (Supercritical Fluid Chromatography with Packed Columns), pp. 223-249 and references cited therein.) In the relevant examples herein, columns were obtained from Chiral Technologies, Inc, West Chester, Pa., USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

For administration to human patients, the total daily dose of a compound of formula (I) is typically in the range of 0.01 mg to 500 mg depending, of course, on the mode of administration. In another embodiment of the present invention, the total daily dose of a compound of formula (I) is typically in the range of 0.1 mg to 300 mg. In yet another embodiment of the present invention, the total daily dose of a compound of formula (I) is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly. In the case of aerosols, the dosage unit is determined by means of a valve which delivers a metered amount. Units in accordance with the invention are typically arranged to administer a metered dose or "puff" containing from 0.001 mg to 10 mg of a compound of the invention. The overall daily dose will typically be in the range 0.001 mg to 40 mg which may be administered in a single dose or, more usually, as divided doses throughout the day.

A compound of formula (I) can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Compounds of formula (I) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

Compounds of formula (I) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound of formula (I) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I) may also be administered directly to the eye or ear, typically in the form of drops of a micronised suspension or solution in isotonic, pH-adjusted, sterile saline.

Compounds of formula (I) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148.

Inasmuch as it may be desirable to administer a combination of active compounds, for example, for the purpose of treating a particular disease or condition, it is within the scope of the present invention that two or more pharmaceutical compositions, at least one of which contains a compound of formula (I), may conveniently be combined in the form of a kit suitable for coadministration of the compositions. Thus, a kit of the invention comprises two or more separate pharmaceutical compositions, at least one of which contains a compound of formula (I), and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

All the compound of formula (I) can be made by the specific and general experimental procedures described below in combination with the common general knowledge of one skilled in the art (see, for example, Comprehensive Organic Chemistry, Ed. Barton and Ollis, Elsevier; Comprehensive Organic Transformations: A Guide to Functional Group Preparations, Larock, John Wiley and Sons).

Methods for Preparing Aryl Pyrimidine Linked Compounds

Those skilled in the art will appreciate that there are many known ways of preparing aryl pyrimidine linked compounds. Such methods are disclosed in patent textbooks and laboratory handbooks which constitute the common general knowledge of the skilled person, including the textbooks referenced above and references cited therein. Typically, an aryl halide (Cl, Br, I) or trifluoromethanesulphonate is stirred with an organometallic species such as a stannane, organomagnesium derivative or a boronate ester or boronic acid in the presence of a catalyst, usually a palladium derivative between 0° C. and 120° C. in solvents including tetrahydrofuran, toluene, DMF and water for 1 to 24 hours. For example, an aryl bromide may be heated to 100° C. in a mixture of water/toluene with a base such as sodium carbonate or sodium hydroxide, a palladium catalyst such as tetrakis(triphenylphosphine)palladium (0), a phase transfer catalyst such as tetra-n-butyl ammonium bromide and an aryl boronic acid or ester. As a second example, an aryl boronic ester an aryl halide (Cl, Br, I) or aryl trifluoromethanesulphonate and a fluoride source such as KF or CsF in a non-aqueous reaction medium such as dioxin may be employed.

Alternatively, an aryl amidine may be combined with a malondialdehyde derivative. One or both of the malondialdehyde carbonyls may be protected as an acetal or other suitable protecting group as defined in 'Protective groups in organic synthesis' by Theodora Greene. The malondialdehyde derivative must contain a carboxylic acid, a protected carboxylic acid or a functionality that may be converted to a carboxylic acid by methodologies known to those skilled in the art on the carbon between the two aldehydes or protected aldehyde functionalities. Typically, the substituted benzamidine, optionally as a salt, is heated with the malondialdehyde derivative in a solvent such as dimethylformamide, dimethylsulfoxide, toluene or n-butanol at a temperature of from 20° C. to 150° C. For example an aryl amidine hydrochloride salt may be heated with methyl-2-(dimethoxymethyl)-3-hydroxyacrylate or methyl 2-formyl-3,3-dimethoxypropanoate in DMF at 100° C.

General Scheme for the Preparation of Amides

Those skilled in the art will appreciate that there are many known ways of preparing amides. For example, see Montalbetti, C. A. G. N and Falque, V., *Amide bond formation and peptide Coupling*, Tetrahedron, (2005) 61: (46), pp. 10827-10852 and references cited therein. The examples provided herein are thus not intended to be exhaustive, but merely illustrative. The general scheme for amide formation is as follows:

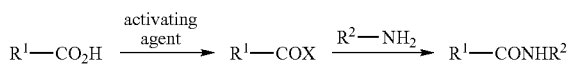

In the following Examples, unless otherwise stated, the following general method was used: To the carboxylic acid (0.15 mmol) and 1-hydroxybenzotriazole (0.3 mmol) in DMF (1.0 mL) was added 0.3.mmol of PS-Carbodiimide resin (Argonaut, 1.3 mmol/g). The mixture was shaken for 10 min and then the amine (0.1 mmol) in DMF (1 mL) was added. The mixture was allowed to agitate overnight at rt and subsequently treated with 0.60 mmole of PS-trisamine (Argonaut, 3.8 mmol/g). Reaction mixture was filtered, concentrated in vacuo and purified by reverse phase chromatography.

Where it is stated that compounds were prepared in the manner described for an earlier Example, the skilled person will appreciate that reaction times, number of equivalents of reagents and reaction temperatures may be modified for each specific reaction, and that it may nevertheless be necessary or desirable to employ different work-up or purification conditions.

Preparation of
1-(2,2,2-trifluoroethyl)piperidin-4-amine

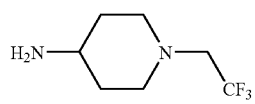

Step A: 8-(Trifluoroacetyl)-1,4-dioxa-8-azaspiro[4.5]decane

4-Piperidone ethylene ketal (127.0 g, 0.887 mol), Et$_3$N (145 mL, 1.044 mol), and 4-dimethylaminopyridine (DMAP, 10.5 g, 0.086 mol) were mixed in dichloromethane (1 L). A solution of trifluoroacetic anhydride (192.0 g, 0.91 mol) in dichloromethane (500 mL) was added dropwise at 0-5° C. for 1 h. The mixture was allowed to warm up to room temperature and stirred overnight. The reaction mixture was washed with 1 N aqueous HCl (2×1.2 L), water (1.2 L), 10% aqueous NaHCO$_3$ (1.2 L), brine (600 mL), dried over anhydrous Na$_2$SO$_4$, and evaporated under vacuum to afford 8-(trifluoroacetyl)-1,4-dioxa-8-azaspiro[4.5]decane (194.5 g).

Step B: 1-(2,2,2-Trifluoroethyl)piperidin-4-one

A solution of 8-(trifluoroacetyl)-1,4-dioxa-8-azaspiro[4.5]decane (87.0 g, 0.364 mol) in THF (375 mL) was added dropwise under argon to 1 M BH$_3$ in THF (800 mL, 0.8 mol) at 0-5° C. for 10 min. The cooling bath was removed. The reaction mixture was refluxed for 5 h, cooled to 0-5° C., and quenched by adding carefully 6 N aqueous HCl (130 mL) for ~1 hour under stirring. The organic solvents were removed under vacuum. The aqueous residue was alkalized with a 50% solution of NaOH (150 mL), diluted with water (500 mL), and extracted with ether (3×400 mL). The combined extracts were dried over anhydrous Na$_2$SO$_4$ and evaporated to give a mixture (98.8 g) of the intermediate 8-(2,2,2-trifluoroethyl)-1,4-dioxa-8-azaspiro[4.5]decane and butanol in 79:21 weight ratio. Water (1.1 L) and concentrated HCl (100 mL) were added, and the obtained mixture was refluxed for 3 h. After cooling to room temperature, the reaction mixture was alkalized to pH 9 by adding a 40% solution of NaOH (~150 mL) and extracted with ether (3×350 mL). The combined extracts were dried over anhydrous Na$_2$SO$_4$ and evaporated to afford a mixture (72.8 g) of 1-(2,2,2-trifluoroethyl)piperidin-4-one and butanol in 86:14 weight ratio.

Step C: 1-(2,2,2-Trifluoroethyl)piperidin-4-amine

A 25% aqueous solution of ammonia (170 mL), 10% Pd/C (7.4 g), and a solution of the above 1-(2,2,2-trifluoroethyl)piperidin-4-one/butanol mixture (72.5 g, 0.344 mol, 86:14 weight ratio) in methanol (420 mL) were placed into a 2 L glass autoclave purged with argon. The reaction mixture was hydrogenated in a Parr apparatus at a hydrogen pressure of 40 psi for 18 h. The catalyst was removed by filtration. The filtrate was concentrated in vacuo to 150 mL. Potash (46 g) and ether (200 mL) were added, and the mixture was vigorously stirred for 20 min. The organic layer was separated, and the aqueous one was extracted with ether (100 mL). The combined organic layers were dried over anhydrous Na$_2$SO$_4$ and evaporated to afford a mixture (74.4 g) of 1-(2,2,2-trifluoroethyl)piperidin-4-amine and 1-(2,2,2-trifluoroethyl)-N-[1-(2,2,2-trifluoroethyl)piperidin-4-yl]piperidin-4-amine in 72:28 weight ratio (containing butanol). This mixture was fractionated at 7-8 mmHg on a 15 cm Vigreaux column (a fraction with bp 75-95° C. was collected) to afford 1-(2,2,2-trifluoroethyl)piperidin-4-amine (38.5 g) as a colorless liquid.

The following compounds of formula (VI) were made according to the general scheme for amide sythesis described above.

(VI)

Structure: 2-phenyl-4-methylpyrimidine-5-carboxamide linked to piperidin-4-yl with N-substituent Q.

| Ex | Q | Name | MS calc (M+H) | MS obs (M+H) |
|---|---|---|---|---|
| 1 | isopropyl | N-(1-Isopropylpiperidin-4-yl)-4-methyl-2-phenylpyrimidine-5-carboxamide | 339.2185 | 339.2191 |
| 2 | benzyl | N-(1-Benzylpiperidin-4-yl)-4-methyl-2-phenylpyrimidine-5-carboxamide | 387.2185 | 387.2150 |
| 3 | (pyridin-2-yl)methyl | 4-Methyl-2-phenyl-N-[1-(pyridin-2-ylmethyl)piperidin-4-yl]pyrimidine-5-carboxamide | 388.2137 | 388.2115 |
| 4 | CH₃ | 4-Methyl-N-(1-methylpiperid-4-yl)-2-phenylpyrimidine-5-carboxamide | 311.1872 | 311.1879 |
| 5 | butyryl | N-(1-Butyrylpiperidin-4-yl)-4-methyl-2-phenylpyrimidine-5-carboxamide | 367.2134 | 367.2135 |
| 6 | ethoxycarbonyl | Ethyl 4-{[(4-methyl-2-phenylpyrimidin-5-yl)carbonyl]amino}piperidine-1-carboxylate | 369.1927 | 369.1996 |
| 7 | (tetrahydro-2H-pyran-4-yl)methyl | 4-Methyl-2-phenyl-N-[1-(tetrahydro-2H-pyran-4-ylmethyl)piperidin-4-yl]pyrimidine-5-carboxamide | 395.2447 | 395.2437 |

The following compounds of formula (III) were made according to the general scheme for amide sythesis described above.

(III)

Structure: 2-phenylpyrimidine-5-carboxamide linked to piperidin-4-yl with N-substituent Q.

| Ex | Q | Name | MS calc (M+H) | MS obs (M+H) |
|---|---|---|---|---|
| 8 | (pyridin-2-yl)methyl | 2-Phenyl-N-[1-(pyridin-2-ylmethyl)piperidin-4-yl]pyrimidine-5-carboxamide | 374.1981 | 374.1985 |
| 9 | CH₂CF₃ | 2-Phenyl-N-[1-(2,2,2-trifluoroethyl)piperidin-4-yl]pyrimidine-5-carboxamide | 364.1637 | 364.1584 |
| 10 | propyl | 2-Phenyl-N-(1-propylpiperidin-4-yl)pyrimidine-5-carboxamide | 325.2028 | 325.2010 |
| 11 | isobutyl | N-(1-Isobutylpiperidin-4-yl)-2-phenylpyrimidine-5-carboxamide | 339.2185 | 339.2159 |
| 12 | benzyl | N-(1-Benzylpiperidin-4-yl)-2-phenylpyrimidine-5-carboxamide | 373.2 | 373.1 |
| 13 | isopropyl | N-(1-Isopropylpiperidin-4-yl)-2-phenylpyrimidine-5-carboxamide | 325.2028 | 325.2043 |
| 14 | 2,6-dimethoxybenzyl | N-[1-(2,6-Dimethoxybenzyl)piperidin-4-yl]-2-phenylpyrimidine-5-carboxamide | 433.2240 | 433.2169 |

The following compounds of formula (IV) were made according to the general scheme for amide sythesis described above.

(IV)

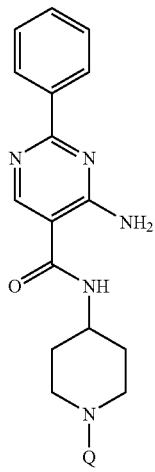

| Ex | Q | Name | MS calc (M + H) | MS obs (M + H) |
|---|---|---|---|---|
| 15 | isobutyl (CH2CH(CH3)2) | 4-Amino-N-(1-isobutylpiperidin-4-yl)-2-phenyl-pyrimidine-5-carboxamide | 354.2294 | 354.2291 |
| 16 | isopropyl (CH(CH3)2) | 4-Amino-N-(1-isopropylpiperidin-4-yl)-2-phenyl-pyrimidine-5-carboxamide | 340.2137 | 340.2151 |
| 17 | 2,6-dimethoxybenzyl | 4-Amino-N-[1-(2,6-dimethoxybenzyl)piperidin-4-yl]-2-phenylpyrimidine-5-carboxamide | 448.2349 | 448.2359 |
| 18 | pyridin-2-ylmethyl | 4-Amino-2-phenyl-N-[1-(pyridin-2-ylmethyl)piperidin-4-yl]pyrimidine-5-carboxamide | 389.2090 | 389.2075 |

The following compounds of formula (V) were made according to the general scheme for amide sythesis described above.

(V)

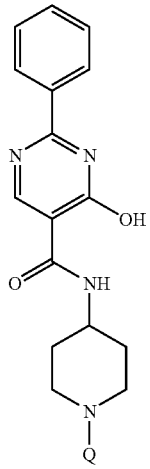

| Ex | Q | Name | MS calc (M + H) | MS obs (M + H) |
|---|---|---|---|---|
| 19 | benzyl | N-(1-Benzylpiperidin-4-yl)-4-hydroxy-2-phenylpyrimidine-5-carboxamide | 389.1978 | 389.1950 |
| 20 | CH2-C(=O)-O-C(CH3)3 (Boc-like) | tert-Butyl 4-{[(4-hydroxy-2-phenyl-pyrimidin-5-yl)carbonyl]amino}piperidine-1-carboxylate | 399.2032 | 399.2030 |
| 21 | pyridin-2-ylmethyl | 4-Hydroxy-2-phenyl-N-[1-(pyridin-2-ylmethyl)piperidin-4-yl]pyrimidine-5-carboxamide | 390.1930 | 390.1859 |
| 22 | 2,2,2-trifluoroethyl | 4-Hydroxy-2-phenyl-N-[1-(2,2,2-trifluoroethyl)piperidin-4-yl]pyrimidine-5-carboxamide | 381.1538 | 381.1529 |
| 23 | 2,6-dimethoxybenzyl | N-[1-(2,6-Dimethoxybenzyl)piperidin-4-yl]-4-hydroxy-2-phenyl-pyrimidine-5-carboxamide | 449.2189 | 449.2162 |
| 24 | isopropyl (CH(CH3)2) | 4-Hydroxy-N-(1-isopropylpiperidin-4-yl)-2-phenyl pyrimidine-5-carboxamide | 341.1978 | 341.2020 |

The following compounds of formula (III) were made according to the general scheme for amide sythesis described above.

(III)

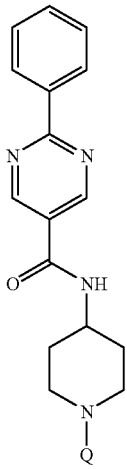

EXAMPLE 25

2-(3-Fluorophenyl)-N-{1-[(methylamino)carbonyl]piperidin-4-yl}pyrimidine-5-carboxamide

Q=

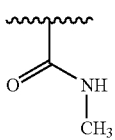

¹H NMR (400 MHz, DMSO-d6) δ ppm 9.26 (2 H, s), 8.65 (1 H, d, J=7.7 Hz), 8.29 (1 H, d, J=7.9 Hz), 8.10-8.19 (1 H, m), 7.57-7.69 (1 H, m), 7.38-7.51 (1 H, m), 6.46 (1 H, d, J=4.3 Hz), 3.87-4.07 (3 H, m), 2.74-2.88 (1 H, m), 2.57 (3 H, d, J=4.3 Hz), 1.79 (2 H, br. s.), 1.43 (2 H, br. s.), 1.18-1.31 (2 H, m).
MS calc (M+H) 358.16; MS obs (M+H) 358.3.

EXAMPLE 26

2-(3-Fluorophenyl)-N-(1-pyridazin-3-ylpiperidin-4-yl)pyrimidine-5-carboxamide

Q=

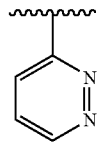

1H NMR (400 MHz, DMSO-d6) δ ppm 9.27 (2 H, s), 8.69 (1 H, d, J=7.7 Hz), 8.54 (1 H, dd, J=4.4, 1.3 Hz), 8.29 (1 H, d, J=7.9 Hz), 8.11-8.18 (1 H, m), 7.57-7.69 (1 H, m), 7.41-7.48 (1 H, m), 7.35-7.41 (1 H, m), 7.29-7.35 (1 H, m), 4.39 (2 H, d, J=13.3 Hz), 4.10-4.25 (1 H, m), 3.04-3.19 (2 H, m), 1.89-2.00 (2 H, m), 1.49-1.67 (1 H, m), 1.19-1.31 (1 H, m).
MS calc (M+H) 379.16; MS obs (M+H) 379.4.

EXAMPLE 27

2-(3-Fluorophenyl)-N-[1-(2,2,2-trifluoroethyl)piperidin-4-yl]pyrimidine-5-carboxamide

Q=

1H NMR (400 MHz, METHANOL-d₄) δ ppm 1.72-1.86 (m, 2 H) 2.02 (br. s., 2 H) 2.72 (br. s., 2H) 3.18 (br. s., 2 H) 3.30-3.41 (m, 2 H) 3.97 (br. s., 1 H) 7.20-7.33 (m, 1 H) 7.47-7.57 (m, 1 H) 8.13-8.21 (m, 1 H) 8.31 (d, J=7.79 Hz, 1 H) 9.19 (s, 2 H).
MS calc (M+H) 383.1495; MS obs (M+H) 383.1514.

| Ex | Q | Name | MS calc (M + H) | MS obs (M + H) |
|---|---|---|---|---|
| 28 |  | N-{1-[2-(4-Cyano-3-fluorophenoxy)-1-phenylethyl]piperidin-4-yl}-2-(3-fluorophenyl)pyrimidine-5-carboxamide | 540.21 | 540.8 |
| 29 | | N-{1-[2-(2-Chloro-6-fluorophenoxy)-1-phenylethyl]piperidin-4-yl}-2-(3-fluorophenyl)pyrimidine-5-carboxamide | 549.18 | 549.5 |

-continued

| Ex | Q | Name | MS calc (M + H) | MS obs (M + H) |
|---|---|---|---|---|
| 30 | | N-{1-[2-(2,6-Difluorophenoxy)-1-phenylethyl]piperidin-4-yl}-2-(3-fluorophenyl)pyrimidine-5-carboxamide | 533.21 | 533.5 |
| 31 | | N-{1-[2-(4-Cchloro-2-cyanophenoxy)-1-phenylethyl]piperidin-4-yl}-2-(3-fluorophenyl)pyrimidine-5-carboxamide | 556.18 | 556.5 |
| 32 | | 2-(3-Fluorophenyl)-N-{1-[1-phenyl-2-(2,4,6-trifluorophenoxy)ethyl]piperidin-4-yl}pyrimidine-5-carboxamide | 551.2 | 551.7 |
| 33 | | N-{1-[2-(3-Chloro-2,6-difluorophenoxy)-1-phenylethyl]piperidin-4-yl}-2-(3-fluorophenyl)pyrimidine-5-carboxamide | 567.17 | 567.5 |
| 34 | | N-{1-[2-(3,5-Difluorophenoxy)-1-phenylethyl]piperidin-4-yl}-2-(3-fluorophenyl)pyrimidine-5-carboxamide | 533.21 | 533.5 |
| 35 | | N-[1-(Cyclopropylmethyl)piperidin-4-yl]-2-(3-fluorophenyl)pyrimidine-5-carboxamide | 355.19 | 355.3 |
| 36 | | 2-(3-Fluorophenyl)-N-{1-[4-(trifluoromethoxy)benzyl]piperidin-4-yl}pyrimidine-5-carboxamide | 475.17 | 475.5 |

-continued

| Ex | Q | Name | MS calc (M + H) | MS obs (M + H) |
|---|---|---|---|---|
| 37 | | 2-(3-Fluorophenyl)-N-{1-[3-fluoro-4-(trifluoromethyl)benzyl]piperidin-4-yl}pyrimidine-5-carboxamide | 477.16 | 477.5 |
| 38 | | 2-(3-Fluorophenyl)-N-[1-(2-phenoxy-1-phenylethyl)piperidin-4-yl]pyrimidine-5-carboxamide | 497.23 | 497.9 |
| 39 | | 2-(3-Fluorophenyl)-N-{1-[2-(3-methoxyphenoxy)-1-phenylethyl]piperidin-4-yl}pyrimidine-5-carboxamide | 527.24 | 527.8 |
| 40 | | N-{1-[2-(3-Cyanophenoxy)-1-phenylethyl]piperidin-4-yl}-2-(3-fluorophenyl)pyrimidine-5-carboxamide | 522.22 | 522.7 |
| 41 | | N-{1-[2-(3-Chlorophenoxy)-1-phenylethyl]piperidin-4-yl}-2-(3-fluorophenyl)pyrimidine-5-carboxamide | 531.19 | 531.5 |
| 42 | | N-{1-[2-(3-Chloro-4-fluorophenoxy)-1-phenylethyl]piperidin-4-yl}-2-(3-fluorophenyl)pyrimidine-5-carboxamide | 549.18 | 549.5 |
| 43 | | N-{1-[2-(6-Chloro-2-fluoro-3-methylphenoxy)-1-phenylethyl]piperidin-4-yl}-2-(3-fluorophenyl)pyrimidine-5-carboxamide | 563.19 | 563.5 |

-continued

| Ex | Q | Name | MS calc (M + H) | MS obs (M + H) |
|---|---|---|---|---|
| 44 | (4-fluorophenoxy-CH2-CH(Ph)-) | N-{1-[2-(4-Fluorophenoxy)-1-phenylethyl]piperidin-4-yl}-2-(3-fluorophenyl)pyrimidine-5-carboxamide | 515.22 | 515.8 |
| 45 | (4-fluoro-3-methylphenoxy-CH2-CH(Ph)-) | N-{1-[2-(4-Fluoro-3-methylphenoxy)-1-phenylethyl]piperidin-4-yl}-2-(3-fluorophenyl)pyrimidine-5-carboxamide | 529.23 | 529.7 |
| 46 | (4-ethylphenoxy-CH2-CH(Ph)-) | N-{1-[2-(4-Ethylphenoxy)-1-phenylethyl]piperidin-4-yl}-2-(3-fluorophenyl)pyrimidine-5-carboxamide | 525.26 | 525.8 |
| 47 | (2,4-difluorophenoxy-CH2-CH(Ph)-) | N-{1-[2-(2,4-Difluorophenoxy)-1-phenylethyl]piperidin-4-yl}-2-(3-fluorophenyl)pyrimidine-5-carboxamide | 533.21 | 533.5 |
| 48 | (4-trifluoromethylphenoxy-CH2-CH(Ph)-) | 2-(3-Fluorophenyl)-N-(1-{1-phenyl-2-[4-(trifluoromethyl)phenoxy]ethyl}piperidin-4-yl)pyrimidine-5-carboxamide | 565.21 | 565.5 |
| 49 | (3,4-difluorophenoxy-CH2-CH(Ph)-) | N-{1-[2-(3,4-Difluorophenoxy)-1-phenylethyl]piperidin-4-yl}-2-(3-fluorophenyl)pyrimidine-5-carboxamide | 533.21 | 533.5 |
| 50 | (3,4,5-trifluorophenoxy-CH2-CH(Ph)-) | 2-(3-Fluorophenyl)-N-{1-[1-phenyl-2-(3,4,5-trifluorophenoxy)ethyl]piperidin-4-yl}pyrimidine-5-carboxamide | 551.2 | 551.7 |

-continued

| Ex | Q | Name | MS calc (M + H) | MS obs (M + H) |
|---|---|---|---|---|
| 51 | 2,5-difluorophenoxymethyl-phenylethyl group | N-{1-[2-(2,5-Difluorophenoxy)-1-phenylethyl]piperidin-4-yl}-2-(3-fluorophenyl)pyrimidine-5-carboxamide | 533.21 | 533.5 |
| 52 | cyclohexylmethyl group | N-[1-(Cyclohexylmethyl)piperidin-4-yl]-2-(3-fluorophenyl)pyrimidine-5-carboxamide | 397.23 | 397.3 |
| 53 | 2-phenyl-2-(2,3-difluorophenoxymethyl)ethyl group | N-{1-[2-(2,3-Difluorophenoxy)-1-phenylethyl]piperidin-4-yl}-2-(3-fluorophenyl)pyrimidine-5-carboxamide | 533.21 | 533.5 |
| 54 | 2-methoxyphenoxymethyl-phenylethyl group | 2-(3-Fluorophenyl)-N-{1-[2-(2-methoxyphenoxy)-1-phenylethyl]piperidin-4-yl}pyrimidine-5-carboxamide | 527.24 | 527.8 |
| 55 | 2,3,4-trifluorophenoxymethyl-phenylethyl group | 2-(3-Fluorophenyl)-N-{1-[1-phenyl-2-(2,3,4-trifluorophenoxy)ethyl]piperidin-4-yl}pyrimidine-5-carboxamide | 551.2 | 551.7 |
| 56 | 3,4-dimethylphenoxymethyl-phenylethyl group | N-{1-[2-(3,4-Dimethylphenoxy)-1-phenylethyl]piperidin-4-yl}-2-(3-fluorophenyl)pyrimidine-5-carboxamide | 525.26 | 525.8 |
| 57 | 4-fluoro-2-methylphenoxymethyl-phenylethyl group | N-{1-[2-(4-Fluoro-2-methylphenoxy)-1-phenylethyl]piperidin-4-yl}-2-(3-fluorophenyl)pyrimidine-5-carboxamide | 529.23 | 529.8 |

-continued

| Ex | Q | Name | MS calc (M + H) | MS obs (M + H) |
|---|---|---|---|---|
| 58 | 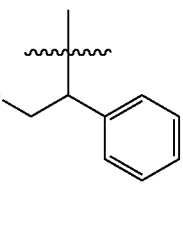 | 2-(3-Fluorophenyl)-N-{1-[2-(4-methoxyphenoxy)-1-phenylethyl]piperidin-4-yl}pyrimidine-5-carboxamide | 527.24 | 527.8 |
| 59 | 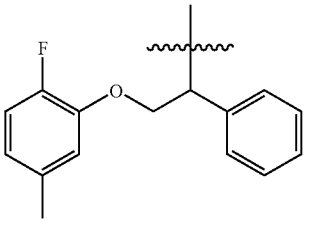 | N-{1-[2-(2-Fluoro-5-methylphenoxy)-1-phenylethyl]piperidin-4-yl}-2-(3-fluorophenyl)pyrimidine-5-carboxamide | 529.23 | 529.7 |
| 60 | 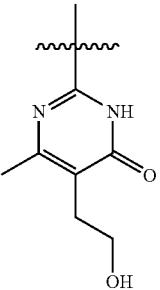 | 2-(3-Fluorophenyl)-N-{1-[5-(2-hydroxyethyl)-4-methyl-6-oxo-1,6-dihydropyrimidin-2-yl]piperidin-4-yl}pyrimidine-5-carboxamide | 453.2 | 453.5 |
| 61 | 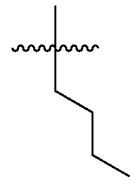 | N-(1-Butylpiperidin-4-yl)-2-(3-fluorophenyl)pyrimidine-5-carboxamide | 357.2 | 357.5 |
| 62 | 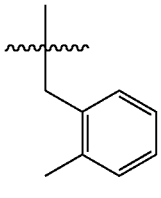 | 2-(3-Fluorophenyl)-N-[1-(2-methylbenzyl)piperidin-4-yl]pyrimidine-5-carboxamide | 405.2 | 405.5 |
| 63 | 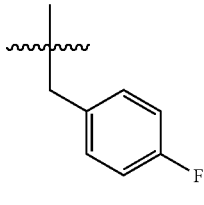 | N-[1-(4-Fluorobenzyl)piperidin-4-yl]-2-(3-fluorophenyl)pyrimidine-5-carboxamide | 409.18 | 409.5 |
| 64 | 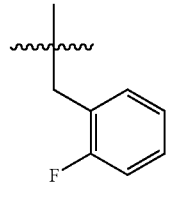 | N-[1-(2-Fluorobenzyl)piperidin-4-yl]-2-(3-fluorophenyl)pyrimidine-5-carboxamide | 409.18 | 409.5 |

-continued

| Ex | Q | Name | MS calc (M + H) | MS obs (M + H) |
|---|---|---|---|---|
| 65 | 3-fluorobenzyl group | N-[1-(3-Fluorobenzyl)piperidin-4-yl]-2-(3-fluorophenyl)pyrimidine-5-carboxamide | 409.18 | 409.6 |
| 66 | cyclopentylmethyl group | N-[1-(Cyclopentylmethyl)piperidin-4-yl]-2-(3-fluorophenyl)pyrimidine-5-carboxamide | 383.22 | 383.5 |
| 67 | 4-(trifluoromethyl)benzyl group | 2-(3-Fluorophenyl)-N-{1-[4-(trifluoromethyl)benzyl]piperidin-4-yl}pyrimidine-5-carboxamide | 459.17 | 459.5 |
| 68 | 1-ethylpropyl group | N-[1-(1-Ethylpropyl)piperidin-4-yl]-2-(3-fluorophenyl)pyrimidine-5-carboxamide | 371.22 | 371.5 |
| 69 | sec-butyl group | N-(1-sec-Butylpiperidin-4-yl)-2-(3-fluorophenyl)pyrimidine-5-carboxamide | 357.2 | 357.5 |
| 70 | 4-methyl-6-oxo-1,6-dihydropyrimidin-2-yl group | 2-(3-Fluorophenyl)-N-[1-(4-methyl-6-oxo-1,6-dihydropyrimidin-2-yl)piperidin-4-yl]pyrimidine-5-carboxamide | 409.17 | 409.3 |

The following compounds of formula (II) were made according to the general scheme for amide sythesis described above.

| Ex | A | Name | MS calc (M) | MS obs (M + H) |
|---|---|---|---|---|
| 71 | 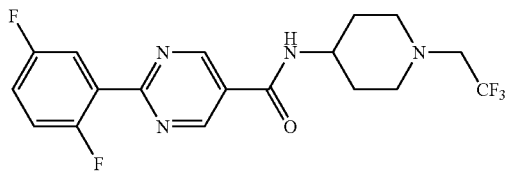 | tert-Butyl (1R,5S,6s)-6-({[2-(3-fluorophenyl)pyrimidin-5-yl]carbonyl}amino)-3-azabicyclo[3.1.0]hexane-3-carboxylate | 398.2 | 343.3 (M-55) |
| 72 | 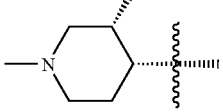 | N-[(3S,4R)-3-Benzyl-1-methylpiperidin-4-yl]-2-(3-fluorophenyl)pyrimidine-5-carboxamide | 404.2 | 405.4 |

EXAMPLE 73

2-(2,5-Difluorophenyl)-N-[1-(2,2,2-trifluoroethyl)piperidin-4-yl]pyrimidine-5-carboxamide Step A: Preparation of methyl 2-(2,5-difluorophenyl)pyrimidine-5-carboxylate To a solution of 2,5-difluorobenzamidine HCl (285 mg, 1.82 mmol) in DMF (8 mL) was added the sodium salt of 3,3-dimethoxy-2-methoxycarbonylpropen-1-ol (419 mg, 2.11 mmol). After heating for 1.5 hr at 100° C. the solution was cooled and H$_2$O (15 mL) was added until a white precipitate formed. The solid was filtered and collected to give the desired product, methyl 2-(2,5-difluorophenyl)pyrimidine-5-carboxylate (40 mg, 16.2%). LC/MS=(M+H)=251.1 observed, 251.06 expected.

Step B: Preparation of 2-(2,5-difluorophenyl)pyrimidine-5-carboxylic acid To a solution of the methyl ester (1.83 g, 8.5 mmol) in THF:H$_2$O:MeOH (8:1:0.5) was added lithium-hydroxide (403 mg, 17 mmol). The solution was stirred at room temperature for ~4 hrs and then acidified. The aqueous mixture was then extracted with ethyl acetate. The organic extracts were dried (Na$_2$SO$_4$) and the solvent removed to give the desired product, 2-(2,5-difluorophenyl)pyrimidine-5-carboxylic acid (1.76, 86%). LC/MS=(M+H)=236.9 observed, 237.05 expected.

Step C: 2-(2,5-difluorophenyl)-N-[1-(2,2,2-trifluoroethyl)piperidin-4-yl]pyrimidine-5-carboxamide To a vial was added 2-(2,5-difluorophenyl)pyrimidine-5-carboxylic acid (47.7 mg, 0.20 mmol), 1-(2,2,2-trifluoroethyl)piperidin-4-amine (36.8 mg, 0.20 mmol), EDAC (42.6 mg, 0.22 mmol), HOBT (27.3 mg, 0.22 mmol), DMA (2 mL) and NMM (0.05 ml, 0.50 mmol). The reactions were stirred overnight at room temperature and then diluted with H$_2$O (4 mL). The resulting precipitate was filtered and washed (3×H$_2$O) to give the desired product. HRMS (M+H) expected=401.1401; observed=401.445.

The following compounds of formula (VII) were prepared using a method analogous to that disclosed above for the preparation of Example 73.

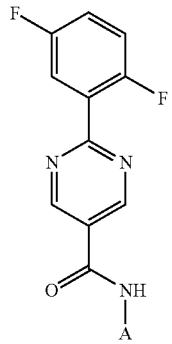

(VII)

| Ex | A | Name | MS calc (M + H) | MS obs (M + H) |
|---|---|---|---|---|
| 74 | 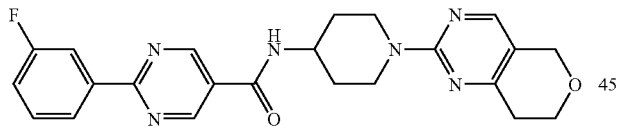 | Ethyl 4-({[2-(2,5-difluorophenyl)pyrimidin-5-yl]carbonyl}amino)piperidine-1-carboxylate | 391.1582 | 391.1631 |
| 75 | 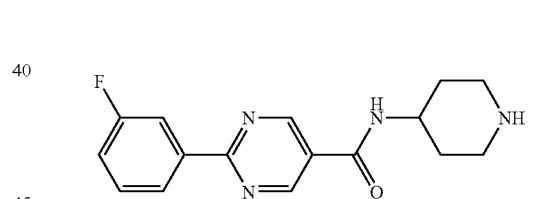 | 2-(2,5-Difluorophenyl)-N-{1-[5-(morpholin-4-ylcarbonyl)pyridin-2-yl]piperidin-4-yl}pyrimidine-5-carboxamide | 509.1 | 509.0 |

EXAMPLE 76

N-[1-(7,8-Dihydro-5H-pyrano[4,3-d]pyrimidin-2-yl)piperidin-4-yl]-2-(3-fluorophenyl)pyrimidine-5-carboxamide To a vial was added 2-(3-fluorophenyl)pyrimidine-5-carboxylic acid (46.4 mg, 0.213 mmol), 1-(7,8-dihydro-5H-pyrano[4,3-d]pyrimidin-2-yl)piperidin-4-amine (50 mg, 0.21 mmol), EDAC (45.0 mg, 0.235 mmol), HOBT (28.8 mg, 0.213 mmol), DMA (1 mL) and NMM (0.058 mL, 0.534 mmol). The reaction was stirred overnight at room temperature and then diluted with water (4 mL) to give a precipitate, which was filtered and collected to give, N-[1-(7,8-dihydro-5H-pyrano[4,3-d]pyrimidin-2-yl)piperidin-4-yl]-2-(3-fluorophenyl)pyrimidine-5-carboxamide (90 mg, 97%). 1H NMR (400 MHz, DMSO-d6) δ ppm 9.23 (2 H, s), 8.60 (1 H, d, J=7.1 Hz), 8.26 (1 H, d, J=7.7 Hz), 8.06-8.15 (2 H, m), 7.59 (1 H, q), 7.41 (1 H, t), 4.49-4.64 (4 H, m), 4.11 (1 H, br. s.), 3.89 (2 H, t, J=5.8 Hz), 3.04 (2 H, t, J=12.4 Hz), 2.66 (2 H, t, J=5.6 Hz), 1.90 (2 H, d, J=12.3 Hz), 1.39-1.55 (2 H, m). HRMS (M+H)=435.1945 expected, 435.2056 observed.

The following Example was prepared analogously to Example 76.

EXAMPLE 77

2-(3-Fluorophenyl)-N-piperidin-4-ylpyrimidine-5-carboxamide

MS (M+H)=300.1 expected, 300.1 observed.

The following compounds of formula (II) were prepared according to the general procedure for amide preparation using the acid 2-(3-fluorophenyl)pyrimidine-5-carboxylic acid.

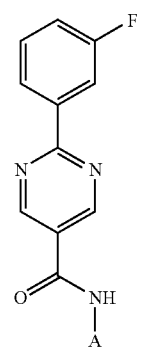

(II)

EXAMPLE 78

2-(3-Fluorophenyl)-N-[1-(6-methyl-5,6,7,8-tetrahydropyrido[4,3-d]pyrimidin-2-yl)pyrrolidin-3-yl]pyrimidine-5-carboxamide

A=

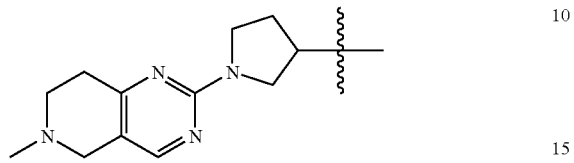

1H NMR (400 MHz, DMSO-d6) δ ppm 9.28 (2 H, s), 8.99 (1 H, d, J=6.5 Hz), 8.29 (1 H, d, J=7.9 Hz), 8.11-8.18 (1 H, m), 8.09 (1 H, s), 7.57-7.68 (1 H, m), 7.40-7.48 (1 H, m), 4.54-4.63 (1H, m), 3.81 (1 H, dd, J=11.5, 6.6 Hz), 3.48-3.72 (4 H, m), 3.42 (2 H, br. s.), 2.72 (3 H, br. s.), 2.40 (3 H, s), 2.21-2.31 (1 H, m), 2.01-2.11 (1 H, m).

MS calc (M) 433.2; MS obs (M+H) 434.5.

| Ex | A | Name | MS calc (M) | MS obs (M + H) |
|---|---|---|---|---|
| 79 | | N-[(3R)-1-Benzylpyrrolidin-3-yl]-2-(3-fluorophenyl)pyrimidine-5-carboxamide | 376.2 | 377.4 |
| 80 | | 2-(3-Fluorophenyl)-N-{1-[4-methyl-5-(methylsulfonyl)pyrimidin-2-yl]pyrrolidin-3-yl}pyrimidine-5-carboxamide | 456.1 | 457.5 |
| 81 | | N-[1-(7,8-Dihydro-5H-pyrano[4,3-d]pyrimidin-2-yl)pyrrolidin-3-yl]-2-(3-fluorophenyl)pyrimidine-5-carboxamide | 420.2 | 421.5 |
| 82 | | Ethyl 3-({[2-(3-fluorophenyl)pyrimidin-5-yl]carbonyl}amino)pyrrolidine-1-carboxylate | 358.1 | 359.3 |
| 83 | | N-[1-(3-Chlorobenzyl)-2-oxopyrrolidin-3-yl]-2-(3-fluorophenyl)pyrimidine-5-carboxamide | 424.1 | 425.0 |

-continued

| Ex | A | Name | MS calc (M) | MS obs (M + H) |
|---|---|---|---|---|
| 84 | | 2-(3-Fluorophenyl)-N-{2-oxo-1-[2-(trifluoromethyl)benzyl]pyrrolidin-3-yl}pyrimidine-5-carboxamide | 458.1 | 459.5 |
| 85 | | N-[1-(2-Chloro-3,6-difluorobenzyl)-2-oxopyrrolidin-3-yl]-2-(3-fluorophenyl)pyrimidine-5-carboxamide | 460.1 | 461.5 |
| 86 | | N-[1-(4-Fluoro-3-methylbenzyl)-2-oxopyrrolidin-3-yl]-2-(3-fluorophenyl)pyrimidine-5-carboxamide | 422.2 | 423.4 |
| 87 | | 2-(3-Fluorophenyl)-N-(1-isopropylpyrrolidin-3-yl)pyrimidine-5-carboxamide | 328.2 | 329.4 |
| 88 | | N-[(3R)-1-Acetylpyrrolidin-3-yl]-2-(3-fluorophenyl)pyrimidine-5-carboxamide | 328.1 | 329.4 |
| 89 | | N-[1-(6,7-Dihydro-5H-cyclopenta[d]pyrimidin-2-yl)pyrrolidin-3-yl]-2-(3-fluorophenyl)pyrimidine-5-carboxamide | 404.2 | 405.5 |
| 90 | | N-[1-(2,3-Dihydro-1H-inden-2-yl)-2-oxopyrrolidin-3-yl]-2-(3-fluorophenyl)pyrimidine-5-carboxamide | 416.2 | 417.6 |
| 91 | | N-[1-(3-Butoxypropyl)-2-oxopyrrolidin-3-yl]-2-(3-fluorophenyl)pyrimidine-5-carboxamide | 414.2 | 415.5 |

| Ex | A | Name | MS calc (M) | MS obs (M + H) |
|---|---|---|---|---|
| 92 | ![structure] | tert-Butyl (3S,4S)-3-fluoro-4-({[2-(3-fluorophenyl)pyrimidin-5-yl]carbonyl}amino)pyrrolidine-1-carboxylate | 404.2 | 349.3 (M-55) |
| 93 | ![structure] | N-[(3R)-1-Acetylpyrrolidin-3-yl]-2-(3-fluorophenyl)pyrimidine-5-carboxamide | 328.1 | 329.1 |

EXAMPLES 81a AND EXAMPLE 81b (R)— and (S)—N-(1-(7,8-Dihydro-5H-pyrano[4,3-d]pyrimidin-2-yl)pyrrolidin-3-yl)-2-(3-fluorophenyl)pyrimidine-5-carboxamide

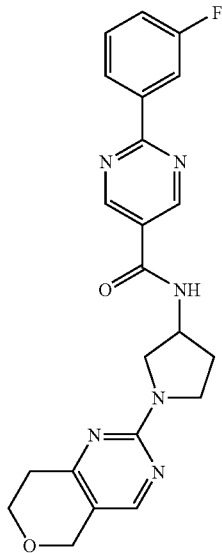

To a round bottom flask containing DMA (10.4 mL) was added 2-(3-fluorophenyl)pyrimidine-5-carboxylic acid (0.91 g, 4.2 mmol), 1-(7,8-dihydro-5H-pyrano[4,3-d]pyrimidin-2-yl)pyrrolidin-3-amine (1.30 g, 4.2 mmol), EDAC (0.88 g, 4.6 mmol) and NMM (1.15 mL, 10.4 mmol). The mixture was stirred at room temperature overnight and then diluted with water (4 mL) to give a precipitate, which was filtered to give the desired racemic product. The racemate was purified by chiral chromatography-SFC (50% EtOH in CO$_2$, OJ-H 30×250 mm column, 70 mL/min) to give two peaks (enantiomeric pair).

Ex. 81a. Peak 1: 0.97 g, $[\alpha]^{25}_D$=+78 (2,2,2-trifluoroethanol, 0.01) where c=g/100 mL; 1H NMR (400 MHz, DMSO-d6) δ ppm 9.24 (2 H, s), 8.95 (1 H, d, J=6.6 Hz), 8.24-8.33 (1 H, m), 8.07-8.15 (1 H, m), 8.06 (1 H, s), 7.52-7.70 (1 H, m), 7.34-7.46 (1 H, m), 4.46-4.65 (3 H, m), 3.88 (2 H, t, J=5.9 Hz), 3.79 (1 H, dd, J=11.5, 6.6 Hz), 3.59-3.68 (1 H, m), 3.43-3.59 (2 H, m), 2.66 (2 H, t, J=5.9 Hz), 2.16-2.32 (1 H, m), 1.97-2.08 (1 H, m).

Ex. 81b. Peak 2: 1.08 g, $[\alpha]^{25}_D$=−78 (2,2,2-trifluoroethanol, 0.01) where c=g/100 mL; 1H NMR (400 MHz, DMSO-d6) δ ppm 9.24 (2 H, s), 8.95 (1 H, d, J=6.6 Hz), 8.26 (1 H, d, J=8.0 Hz), 8.07-8.17 (1 H, m), 8.06 (1 H, s), 7.53-7.63 (1 H, m), 7.32-7.47 (1 H, m), 4.47-4.62 (3 H, m), 3.88 (2 H, t, J=5.8 Hz), 3.78 (1 H, dd, J=11.5, 6.6 Hz), 3.59-3.70 (1 H, m), 3.45-3.59 (2 H, m), 2.66 (2 H, t, J=5.9 Hz), 2.16-2.33 (1 H, m), 1.96-2.09 (1 H, m).

EXAMPLES 82a AND 82b (R)- and (S)-Ethyl 3-(2-(3-fluorophenyl)pyrimidine-5-carboxamido)pyrrolidine-1-carboxylate

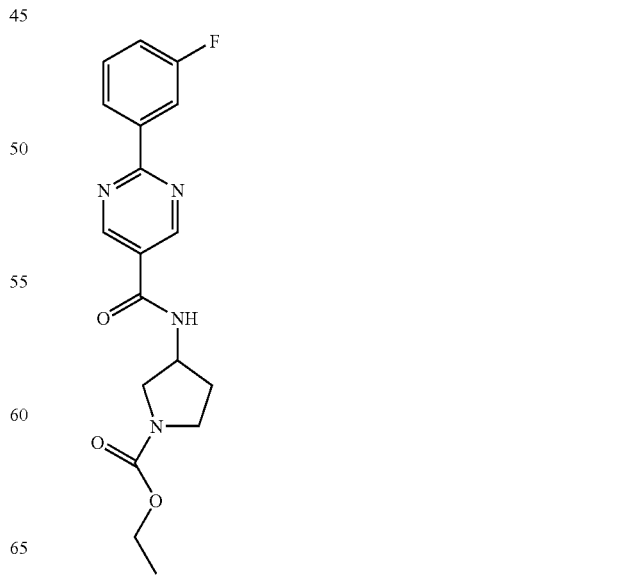

To a round bottom flask containing DMA (10 mL) was added 2-(3-fluorophenyl)pyrimidine-5-carboxylic acid (2.0 g, 9.2 mmol), ethyl 3-aminopyrrolidine-1-carboxylate (1.4 g, 9.2 mmol), HATU (3.49 g, 9.1 mmol) and TEA (0.92 g, 9.1 mmol). The mixture was stirred at room temperature for 5 hrs and then filtered. The filtrate was collected washed with brine (4×), dried (MgSO$_4$) and the solvent removed to give a residue, which was purified by chromatography (silica, 45% etoac/heptane) to give the desired racemic product (1.0 g, 30%). LC/MS (M+H)=359.1 expected, 359.1 observed. The racemate was purified by chiral chromatography-SFC (50% EtOH in CO$_2$, OJ-H, 30×250 mm column, 70 mL/min) to give two peaks (enantiomeric pair).

Ex. 82a. Peak 1: wt=0.47 g; 1H NMR (400 MHz, DMSO-d$_6$) δ ppm 9.24-9.30 (2 H, m), 8.95 (1 H, d, J=6.5 Hz), 8.29 (1 H, d, J=7.9 Hz), 8.10-8.18 (1 H, m), 7.58-7.69 (1 H, m), 7.40-7.50 (1 H, m), 4.49 (1 H, d, J=5.8 Hz), 3.97-4.12 (2 H, m), 3.55-3.68 (1 H, m), 3.35-3.53 (2 H, m), 3.27-3.35 (1 H, m), 2.08-2.24 (1 H, m), 1.88-2.03 (1 H, m), 1.19 (3 H, t, J=7.0 Hz); [α]$^{25}_D$=−37 (ethanol, 0.01) where c=g/100 mL.

Ex. 82b. Peak 2: wt=0.52 g; 1H NMR (400 MHz, DMSO-d$_6$) δ ppm 9.24-9.30 (2 H, m), 8.95 (1 H, d, J=6.5 Hz), 8.29 (1 H, d, J=7.9 Hz), 8.09-8.19 (1 H, m), 7.57-7.67 (1 H, m), 7.40-7.49 (1 H, m), 4.41-4.54 (1 H, m), 3.97-4.11 (1 H, m), 3.54-3.69 (1 H, m), 3.35-3.52 (2 H, m), 3.27-3.35 (1 H, m), 2.08-2.22 (1 H, m), 1.87-2.03 (1 H, m), 1.18 (3 H, t); [α]$^{25}_D$=+34 (ethanol, 0.01) where c=g/100 mL.

EXAMPLE 94 cis-tert-Butyl 3-(2-(3-fluorophenyl)pyrimidine-5-carboxamido)-4-hydroxypyrrolidine-1-carboxylate

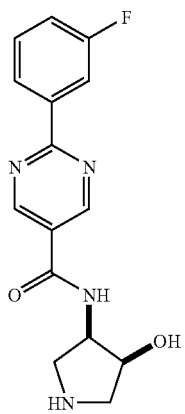

To a solution of 2-(3-fluorophenyl)pyrimidine-5-carboxylic acid (900 mg, 4.12 mmol) in CH$_3$CN/DMF (10 mL/3 mL) was added HATU (1.73 g, 4.54 mmol), DIPEA (1.44 mL, 0.83 mmol) and cis-tert-butyl 3-amino-4-hydroxypyrrolidine-1-carboxylate (918 mg, 4.54 mmol). After 2 hrs, the solvents were removed in vacuo and the residue purified by chromatography (silica, 100% DCM to 5% MeOH/DCM) to give the desired product, cis-tert-butyl 3-(2-(3-fluorophenyl) pyrimidine-5-carboxamido)-4-hydroxypyrrolidine-1-carboxylate (2.33 g, 80%).

LC/MS (M+Na)=425.3 observed, 425.16 expected.

EXAMPLE 95 cis-2-(3-Fluorophenyl)-N-(4-hydroxypyrrolidin-3-yl) pyrimidine-5-carboxamide

To a solution of cis-tert-butyl 3-(2-(3-fluorophenyl)pyrimidine-5-carboxamido)-4-hydroxypyrrolidine-1-carboxylate (1.22 g, 3.03 mmol) in DCM (6 mL) was added TFA (2 mL). The solution stirred at room temperature for 3 hrs and then diluted with toluene (5 mL) and the solvent removed to give a solid, cis-2-(3-fluorophenyl)-N-(4-hydroxypyrrolidin-3-yl)pyrimidine-5-carboxamide-TFA salt (1.26 g, 98%). LC/MS (M+H)=303.1 observed, 303.13 expected.

EXAMPLE 96

2-(3-Fluorophenyl)-N-{(3S,4R)-4-hydroxy-1-[3-(13-thiazol-2-ylcarbonyl)pyridin-2-yl]pyrrolidin-3-yl}pyrimidine-5-carboxamide

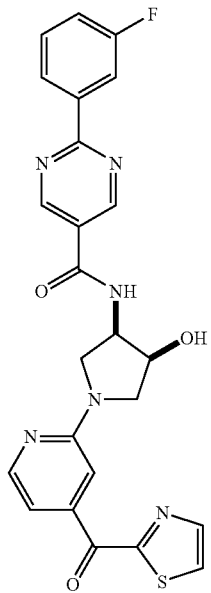

To a vial was added cis-2-(3-fluorophenyl)-N-(4-hydroxy-pyrrolidin-3-yl)pyrimidine-5-carboxamide-TFA salt (50 mg, 0.12 mmol), n-butanol (0.2 mL), TEA (0.016 mL, 0.12 mmol) and (2-chloropyridin-4-yl)(thiazol-2-yl)methanone (40.5 mg, 0.18 mmol. The reaction mixture was heated to 85° C. for 4 hrs and then cooled to rt. The residue mixture was purified by RP-HPLC to give the desired product, cis-2-(3-fluorophenyl)-N-(4-hydroxy-1-(4-(thiazole-2-carbonyl)pyridin-2-yl)pyrrolidin-3-yl)pyrimidine-5-carboxamide (20 mg, 34%). HRMS (M+H) expected=491.1302, observed=491.1357.

The following compounds of formula (II) were prepared using a method analogous to that of Example 96.

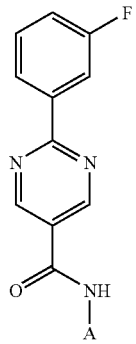

(II)

| Ex | A | Name | MS calc (M + H) | MS obs (M + H) |
|---|---|---|---|---|
| 97 | | Cis-N-{1-[3-(2-Cyanobenzoyl)pyridin-2-yl]-4-hydroxypyrrolidin-3-yl}-2-(3-fluorophenyl)pyrimidine-5-carboxamide | 509.1737 | 509.1756 |
| 98 | | Cis-2-(3-Fluorophenyl)-N-[4-hydroxy-1-pyrimidin-2-ylpyrrolidin-3-yl]pyrimidine-5-carboxamide | 381.1475 | 381.1573 |
| 99 | | Cis-N-{1-[3-(Aminocarbonyl)pyridin-2-yl]-4-hydroxypyrrolidin-3-yl}-2-(3-fluorophenyl)pyrimidine-5-carboxamide | 423.1581 | 423.1693 |

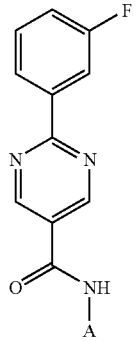

(II)

| Ex | A | Name | MS calc (M + H) | MS obs (M + H) |
|---|---|---|---|---|
| 100 | 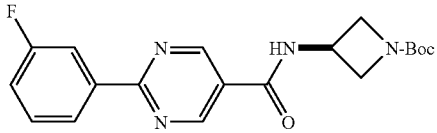 | Cis-N-{1-[3-Cyano-6-(trifluoromethyl)pyridin-2-yl]-4-hydroxypyrrolidin-3-yl}-2-(3-fluorophenyl)pyrimidine-5-carboxamide | 473.1349 | 473.1461 |

EXAMPLE 101 tert-Butyl 3-({[2-(3-fluorophenyl)pyrimidin-5-yl]carbonyl}amino)azetidine-1-carboxylate

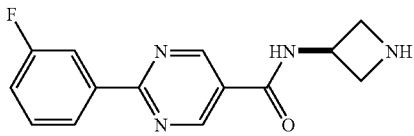

To a solution of acid (0.50 g, 2.30 mmol) in DMF (10 mL) was added HBTU (0.96 g, 2.53 mmol) and DIPEA (0.52 mL, 2.99 mmol). After 1 hr at room temperature, tert-butyl 3-aminoazetidine-1-carboxylate was added and the reaction stirred overnight. The solvent was removed and the residue was partitioned between ethyl acetate and sodium bicarbonate (aqueous saturated). The organic layer was washed with brine (2×), dried (MgSO$_4$), filtered and concentrated to give the desired product, tert-butyl 3-({[2-(3-fluorophenyl)pyrimidin-5-yl]carbonyl}amino)azetidine-1-carboxylate (570 mg, 66%). LC/MS (M+Na+)=395.2 observed, 395.15 expected.

EXAMPLE 102

N-Azetidin-3-yl-2-(3-fluorophenyl)pyrimidine-5-carboxamide

To a solution of tert-butyl 3-({[2-(3-fluorophenyl)pyrimidin-5-yl]carbonyl}amino)azetidine-1-carboxylate (570 mg, 1.53 mmol) in methanol (1 mL) was added 4N HCl in dioxane (3 mL). The reaction mixture was stirred at room temperature overnight and then diluted with ether to give a solid, which was filtered and collected to give the desired product as the hydrochloride salt, N-azetidin-3-yl-2-(3-fluorophenyl)pyrimidine-5-carboxamide (380 mg, 72%). LC/MS (M+H)=273.2 observed, 273.12 expected.

EXAMPLE 103

N-[1-(3-Cyano-4,6-dimethylpyridin-2-yl)azetidin-3-yl]-2-(3-fluorophenyl)pyrimidine-5-carboxamide

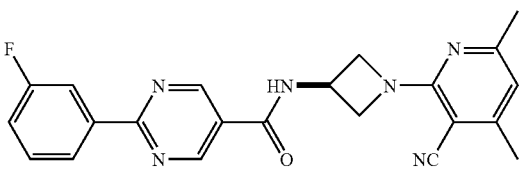

To a vial was added N-azetidin-3-yl-2-(3-fluorophenyl)pyrimidine-5-carboxamide (0.04 g, 0.13 mmol), 2-chloro-4,6-dimethylnicotinonitrile (32.5 mg, 0.19 mmol), and 0.3 mL each of n-butanol, TEA and water. The mixture was heated to 90° C. for 12 hrs and then diluted with ethyl acetate and brine. The layers were separated and the organic layer dried (Na₂SO₄) and the solvent removed to give a solid, which was purified by chromatography (silica, DCM to 1-5% MeOH/DCM) to give the product, N-[1-(3-cyano-4,6-dimethylpyridin-2-yl)azetidin-3-yl]-2-(3-fluorophenyl)pyrimidine-5-carboxamide (52 mg, 76%). HRMS (M+H)=403.1682 expected, 403.1750 observed.

Example 104 and 105 were prepared analogously to Example 103.

EXAMPLE 104

2-(3-Fluorophenyl)-N-[1-(1-phenyl-1H-tetrazol-5-yl)azetidin-3-yl]pyrimidine-5-carboxamide

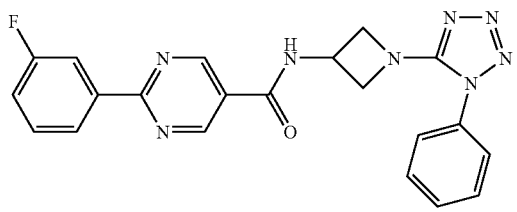

MS calc (M+H) 417.1588; MS obs (M+H) 417.1666.

EXAMPLE 105

2-(3-Fluorophenyl)-N-(1-quinoxalin-2-ylazetidin-3-yl)pyrimidine-5-carboxamide

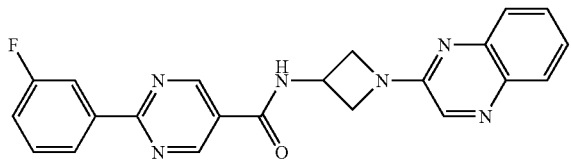

MS calc (M+H) 401.1526; MS obs (M+H) 401.1607.

EXAMPLE 106

N-[1-(2,2-Dimethylpropanoyl)azetidin-3-yl]-2-(3-fluorophenyl)pyrimidine-5-carboxamide

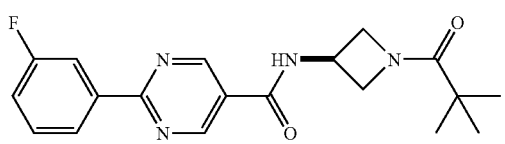

To a solution of N-azetidin-3-yl-2-(3-fluorophenyl)pyrimidine-5-carboxamide (50 mg, 0.16 mmol) in DMF (1.0 mL) was added DIPEA (0.06 mL, 0.32 mmol) and pivaloyl chloride (30 mg, 0.24 mmol). The mixtures were stirred at room temperature overnight. The mixture was partitioned between ethyl acetate and brine. The organic layer was dried (MgSO₄), filtered and concentrated to give a solid, which was purified by chromatography (silica, 80% EtOAc/Hex) to give the product, N-[1-(2,2-dimethylpropanoyl)azetidin-3-yl]-2-(3-fluorophenyl)pyrimidine-5-carboxamide (50 mg, 86%). HRMS (M+H)=357.1727 expected, observed=357.1799.

GENERAL METHOD FOR THE PREPARATION OF EXAMPLES 107-177

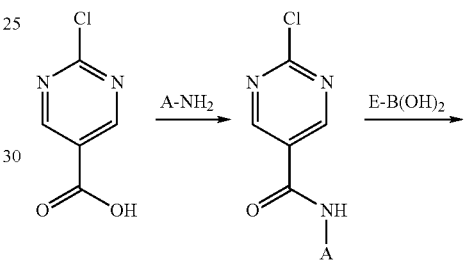

To a vial containing 400 uL of a 0.50 M solution of 2-chloropyrimidine-5-carboxylic acid in DMF was added 840 uL of a 0.25 M DCC/HOAt solution in DMF. The reaction was shaken for 20 minutes and then 420 uL of a 0.50 M solution of amine in DMF was added and the reaction shaken at rt for 30 min to 1 hr. The reaction mixture was then filtered through Baker filter columns into vials.

To the vials was added boronic acid (1 eq), Pd(OAc)₂ (0.04 eq), PS-PPh₃ (0.08 eq) and water (to achieve 5:1 DMF:H₂O). The reaction mixture was heated to 70° C. for ~16 hrs and then cooled to room temperature. The mixtures were filtered and the solvent removed to give a residue, which was purified by RP-HPLC to give the desired product.

The following compounds were prepared using the procedure above:

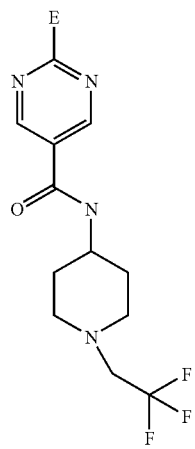

| Ex | E | Name | MS calc (M) | MS obs (M + H) |
|---|---|---|---|---|
| 107 | 2-methylphenyl | 2-(2-Methylphenyl)-N-[1-(2,2,2-trifluoroethyl)piperidin-4-yl]pyrimidine-5-carboxamide | 378.4 | 379.1 |
| 108 | 2-hydroxyphenyl | 2-(2-Hydroxyphenyl)-N-[1-(2,2,2-trifluoroethyl)piperidin-4-yl]pyrimidine-5-carboxamide | 380.4 | 381.1 |
| 109 | 3-hydroxyphenyl | 2-(3-Hydroxyphenyl)-N-[1-(2,2,2-trifluoroethyl)piperidin-4-yl]pyrimidine-5-carboxamide | 380.4 | 381.1 |
| 110 | 2-fluorophenyl | 2-(2-Fluorophenyl)-N-[1-(2,2,2-trifluoroethyl)piperidin-4-yl]pyrimidine-5-carboxamide | 382.4 | 383.1 |
| 111 | 3-cyanophenyl | 2-(3-Cyanophenyl)-N-[1-(2,2,2-trifluoroethyl)piperidin-4-yl]pyrimidine-5-carboxamide | 389.4 | 390.1 |
| 112 | 2-ethylphenyl | 2-(2-Ethyphenyl)-N-[1-(2,2,2-trifluoroethyl)piperidin-4-yl]pyrimidine-5-carboxamide | 392.4 | 393.2 |
| 113 | 2-(hydroxymethyl)phenyl | 2-[2-(Hydroxymethyl)phenyl]-N-[1-(2,2,2-trifluoroethyl)piperidin-4-yl]pyrimidine-5-carboxamide | 394.4 | 395.1 |

-continued

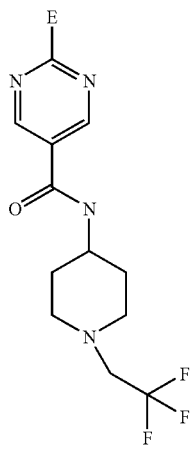

| Ex | E | Name | MS calc (M) | MS obs (M + H) |
|---|---|---|---|---|
| 114 | 2-methoxyphenyl | 2-(2-Methoxyphenyl)-N-[1-(2,2,2-trifluoroethyl)piperidin-4-yl]pyrimidine-5-carboxamide | 394.4 | 395.1 |
| 115 | 3-(hydroxymethyl)phenyl | 2-(3-(Hydroxymethyl)phenyl]-N-[1-(2,2,2-trifluoroethyl)piperidin-4-yl]pyrimidine-5-carboxamide | 394.4 | 395.1 |
| 116 | 2-chlorophenyl | 2-(2-Chlorophenyl)-N-[1-(2,2,2-trifluoroethyl)piperidin-4-yl]pyrimidine-5-carboxamide | 398.8 | 399.1 |
| 117 | 3-chlorophenyl | 2-(3-Chlorophenyl)-N-[1-(2,2,2-trifluoroethyl)piperidin-4-yl]pyrimidine-5-carboxamide | 398.8 | 399.1 |
| 118 | 2,5-difluorophenyl | 2-(2,5-Difluorophenyl)-N-[1-(2,2,2-trifluoroethyl)piperidin-4-yl]pyrimidine-5-carboxamide | 400.4 | 401.1 |
| 119 | 2-acetylphenyl | 2-(2-Acetylphenyl)-N-[1-(2,2,2-trifluoroethyl)piperidin-4-yl]pyrimidine-5-carboxamide | 406.4 | 407.1 |
| 120 | 3-acetylphenyl | 2-(3-Acetylphenyl)-N-[1-(2,2,2-trifluoroethyl)piperidin-4-yl]pyrimidine-5-carboxamide | 406.4 | 407.1 |

-continued

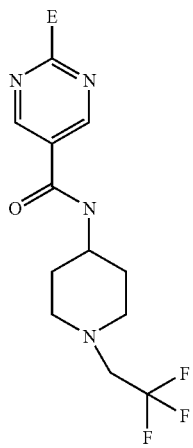

| Ex | E | Name | MS calc (M) | MS obs (M + H) |
|---|---|---|---|---|
| 121 | 3-isopropylphenyl | 2-(3-Isopropylphenyl)-N-[1-(2,2,2-trifluoroethyl)piperidin-4-yl]pyrimidine-5-carboxamide | 406.5 | 407.1 |
| 122 | 2-chloro-5-fluorophenyl | 2-(2-Chloro-5-fluorophenyl)-N-[1-(2,2,2-trifluoroethyl)piperidin-4-yl]pyrimidine-5-carboxamide | 416.8 | 417.1 |
| 123 | 3-acetamidophenyl | 2-[3-(Acetylamino)phenyl]-N-[1-(2,2,2-trifluoroethyl)piperidin-4-yl]pyrimidine-5-carboxamide | 421.4 | 422.2 |
| 124 | 2-(methoxycarbonyl)phenyl | Methyl 2-[5-({[1-(2,2,2-trifluoroethyl)piperidin-4-yl]amino}carbonyl)pyrimidin-2-yl]benzoate | 422.4 | 423.1 |
| 125 | 3-(methoxycarbonyl)phenyl | Methyl 3-[5-({[1-(2,2,2-trifluoroethyl)piperidin-4-yl]amino}carbonyl)pyrimidin-2-yl]benzoate | 422.4 | 423.1 |
| 126 | 2-(trifluoromethyl)phenyl | N-[1-(2,2,2-Trifluoroethyl)piperidin-4-yl]-2-[2-(trifluoromethyl)phenyl]pyrimidine-5-carboxamide | 423.4 | 433.1 |

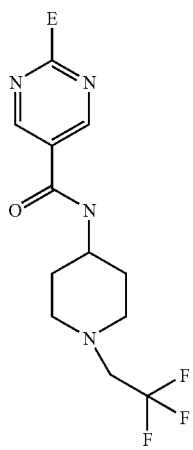

| Ex | E | Name | MS calc (M) | MS obs (M + H) |
|---|---|---|---|---|
| 127 | 3-(trifluoromethyl)phenyl | N-[1-(2,2,2-Trifluoroethyl)piperidin-4-yl]-2-[3-(trifluoromethyl)phenyl]pyrimidine-5-carboxamide | 423.4 | 433.1 |
| 128 | 2-(trifluoromethoxy)phenyl | N-[1-(2,2,2-Trifluoroethyl)piperidin-4-yl]-2-[2-(trifluoromethoxy)phenyl]pyrimidine-5-carboxamide | 448.4 | 449.0 |
| 129 | 3-(trifluoromethoxy)phenyl | N-[1-(2,2,2-Trifluoroethyl)piperidin-4-yl]-2-[3-(trifluoromethoxy)phenyl]pyrimidine-5-carboxamide | 448.4 | 449.1 |
| 130 | 3-(isopropoxycarbonyl)phenyl | Isopropyl 3-[5-({[1-(2,2,2-trifluoroethyl)piperidin-4-yl]amino}carbonyl)pyrimidin-2-yl]benzoate | 450.5 | 451.1 |
| 131 | 3-[(methylsulfonyl)amino]phenyl | 2-{3-[(Methylsulfonyl)amino]phenyl}-N-[1-(2,2,2-trifluoroethyl)piperidin-4-yl]pyrimidine-5-carboxamide | 457.5 | 458.1 |
| 132 | 3-fluorophenyl | 2-(3-Fluorophenyl)-N-[1-(2,2,2-trifluoroethyl)piperidin-4-yl]pyrimidine-5-carboxamide | 382.4 | 383.1 |

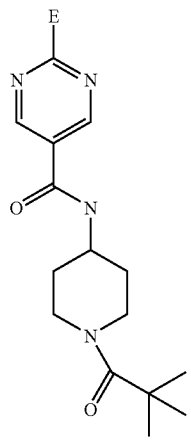

| Ex | E | Name | MS calc (M) | MS obs (M + H) |
|---|---|---|---|---|
| 133 | 2-methylphenyl | N-[1-(2,2-Dimethylpropanoyl)piperidin-4-yl]-2-(2-methylphenyl)pyrimidine-5-carboxamide | 380.5 | 381.2 |
| 134 | 2-hydroxyphenyl | N-[1-(2,2-Dimethylpropanoyl)piperidin-4-yl]-2-(2-hydroxyphenyl)pyrimidine-5-carboxamide | 382.5 | 383.2 |
| 135 | 2-fluorophenyl | N-[1-(2,2-Dimethylpropanoyl)piperidin-4-yl]-2-(2-fluorophenyl)pyrimidine-5-carboxamide | 384.5 | 385.2 |
| 136 | 2-ethylphenyl | N-[1-(2,2-Dimethylpropanoyl)piperidin-4-yl]-2-(2-ethylphenyl)pyrimidine-5-carboxamide | 394.5 | 395.2 |
| 137 | 2-methoxyphenyl | N-[1-(2,2-Dimethylpropanoyl)piperidin-4-yl]-2-(2-methoxyphenyl)pyrimidine-5-carboxamide | 396.5 | 397.2 |
| 138 | 2-chlorophenyl | 2-(2-Chlorophenyl)-N-[1-(2,2-dimethylpropanoyl)piperidin-4-yl]pyrimidine-5-carboxamide | 400.9 | 401.1 |
| 139 | 3-chlorophenyl | 2-(3-Chlorophenyl)-N-[1-(2,2-dimethylpropanoyl)piperidin-4-yl]pyrimidine-5-carboxamide | 400.9 | 401.1 |

-continued

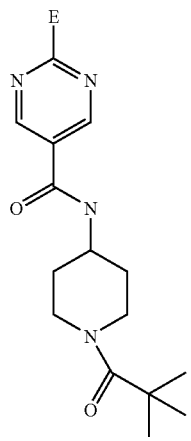

| Ex | E | Name | MS calc (M) | MS obs (M + H) |
|---|---|---|---|---|
| 140 | 2,3-difluorophenyl | 2-(2,3-Difluorophenyl)-N-[1-(2,2-dimethylpropanoyl)piperidin-4-yl]pyrimidine-5-carboxamide | 402.4 | 403.2 |
| 141 | 2,5-difluorophenyl | 2-(2,5-Difluorophenyl)-N-[1-(2,2-dimethylpropanoyl)piperidin-4-yl]pyrimidine-5-carboxamide | 402.4 | 403.2 |
| 142 | 3-acetylphenyl | 2-(3-Acetylphenyl)-N-[1-(2,2-dimethylpropanoyl)piperidin-4-yl]pyrimidine-5-carboxamide | 408.5 | 409.2 |
| 143 | 3-isopropylphenyl | N-[1-(2,2-Dimethylpropanoyl)piperidin-4-yl]-2-(3-isopropylphenyl)pyrimidine-5-carboxamide | 408.5 | 409.2 |
| 144 | 2-chloro-5-fluorophenyl | 2-(2-Chloro-5-fluorophenyl)-N-[1-(2,2-dimethylpropanoyl)piperidin-4-yl]pyrimidine-5-carboxamide | 418.9 | 419.1 |
| 145 | 3-(methoxycarbonyl)phenyl | Methyl 3-[5-({[1-(2,2-dimethylpropanoyl)piperidin-4-yl]amino}carbonyl)pyrimidin-2-yl]benzoate | 424.5 | 425.1 |

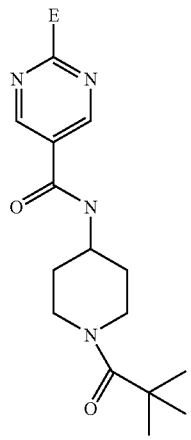

| Ex | E | Name | MS calc (M) | MS obs (M + H) |
|---|---|---|---|---|
| 146 | 2-CF3-phenyl | N-[1-(2,2-Dimethylpropanoyl)piperidin-4-yl]-2-[2-(trifluoromethyl)phenyl]pyrimidine-5-carboxamide | 434.5 | 435.1 |
| 147 | 3-CF3-phenyl | N-[1-(2,2-Dimethylpropanoyl)piperidin-4-yl]-2-[3-(trifluoromethyl)phenyl]pyrimidine-5-carboxamide | 434.5 | 435.1 |
| 148 | 2-OCF3-phenyl | N-[1-(2,2-Dimethylpropanoyl)piperidin-4-yl]-2-[2-(trifluoromethoxy)phenyl]pyrimidine-5-carboxamide | 450.5 | 451.2 |
| 149 | 3-OCF3-phenyl | N-[1-(2,2-Dimethylpropanoyl)piperidin-4-yl]-2-[3-(trifluoromethoxy)phenyl]pyrimidine-5-carboxamide | 450.5 | 451.2 |
| 150 | 3-F-phenyl | N-[1-(22-Dimethylpropanoyl)piperidin-4-yl]-2-(3-fluorophenyl)pyrimidine-5-carboxamide | 382.4 | 383.1 |

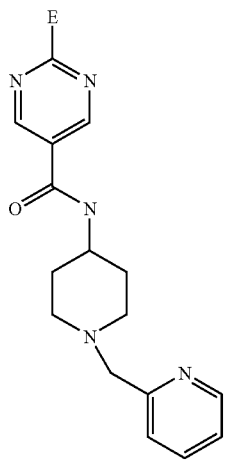

| Ex | E | Name | MS calc (M) | MS obs (M + H) |
|---|---|---|---|---|
| 151 | 2-methylphenyl | 2-(2-Methylphenyl)-N-[1-(pyridin-2-ylmethyl)piperidin-4-yl]pyrimidine-5-carboxamide | 387.5 | 388.2 |
| 152 | 2-hydroxyphenyl | 2-(2-Hydroxyphenyl)-N-[1-(pyridin-2-ylmethyl)piperidin-4-yl]pyrimidine-5-carboxamide | 389.5 | 390.1 |
| 153 | 3-hydroxyphenyl | 2-(3-Hydroxyphenyl)-N-[1-(pyridin-2-ylmethyl)piperidin-4-yl]pyrimidine-5-carboxamide | 389.5 | 390.1 |
| 154 | 2-fluorophenyl | 2-(2-Fluorophenyl)-N-[1-(pyridin-2-ylmethyl)piperidin-4-yl]pyrimidine-5-carboxamide | 391.5 | 392.1 |
| 155 | 3-cyanophenyl | 2-(3-Cyanophenyl)-N-[1-(pyridin-2-ylmethyl)piperidin-4-yl]pyrimidine-5-carboxamide | 398.5 | 399.2 |
| 156 | 2-ethylphenyl | 2-(2-Ethylphenyl)-N-[1-(pyridin-2-ylmethyl)piperidin-4-yl]pyrimidine-5-carboxamide | 401.5 | 402.2 |
| 157 | 2-(hydroxymethyl)phenyl | 2-[2-(Hydroxymethyl)phenyl]-N-[1-(pyridin-2-ylmethyl)piperidin-4-yl]pyrimidine-5-carboxamide | 403.5 | 404.1 |

-continued

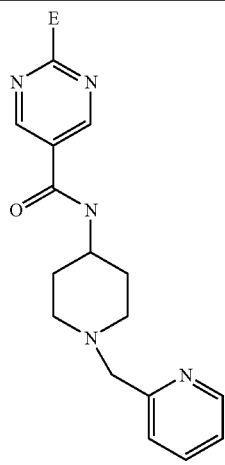

| Ex | E | Name | MS calc (M) | MS obs (M + H) |
|---|---|---|---|---|
| 158 | 2-methoxyphenyl | 2-(2-Methoxyphenyl)-N-[1-(pyridin-2-ylmethyl)piperidin-4-yl]pyrimidine-5-carboxamide | 403.5 | 404.1 |
| 159 | 3-(hydroxymethyl)phenyl | 2-[3-(Hydroxymethyl)phenyl]-N-[1-(pyridin-2-ylmethyl)piperidin-4-yl]pyrimidine-5-carboxamide | 403.5 | 404.2 |
| 160 | 2-chlorophenyl | 2-(2-Chlorophenyl)-N-[1-(pyridin-2-ylmethyl)piperidin-4-yl]pyrimidine-5-carboxamide | 407.9 | 408.1 |
| 161 | 3-chlorophenyl | 2-(3-Chlorophenyl)-N-[1-(pyridin-2-ylmethyl)piperidin-4-yl]pyrimidine-5-carboxamide | 407.9 | 408.1 |
| 162 | 2,3-difluorophenyl | 2-(2,3-Difluorophenyl)-N-[1-(pyridin-2-ylmethyl)piperidin-4-yl]pyrimidine-5-carboxamide | 409.4 | 410.1 |
| 163 | 2,5-difluorophenyl | 2-(2,5-Difluorophenyl)-N-[1-(pyridin-2-ylmethyl)piperidin-4-yl]pyrimidine-5-carboxamide | 409.4 | 410.1 |
| 164 | 2-acetylphenyl | 2-(2-Acetylphenyl)-N-[1-(pyridin-2-ylmethyl)piperidin-4-yl]pyrimidine-5-carboxamide | 415.5 | 416.2 |

-continued

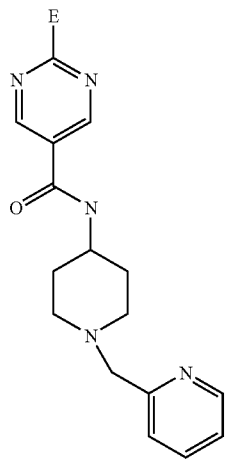

| Ex | E | Name | MS calc (M) | MS obs (M + H) |
|---|---|---|---|---|
| 165 | 3-acetylphenyl | 2-(3-Acetylphenyl)-N-[1-(pyridin-2-ylmethyl)piperidin-4-yl]pyrimidine-5-carboxamide | 415.5 | 416.2 |
| 166 | 3-isopropylphenyl | 2-(3-Isopropylphenyl)-N-[1-(pyridin-2-ylmethyl)piperidin-4-yl]pyrimidine-5-carboxamide | 415.5 | 416.2 |
| 167 | 2-chloro-5-fluorophenyl | 2-(2-Chloro-5-fluorophenyl)-N-[1-(pyridin-2-ylmethyl)piperidin-4-yl]pyrimidine-5-carboxamide | 452.9 | 426.1 |
| 168 | 3-(acetylamino)phenyl | 2-[3-(Acetylamino)phenyl]-N-[1-(pyridin-2-ylmethyl)piperidin-4-yl]pyrimidine-5-carboxamide | 430.5 | 431.2 |
| 169 | 2-(methoxycarbonyl)phenyl | Methyl 2-[5-({[1-(pyridin-2-ylmethyl)piperidin-4-yl]amino}carbonyl)pyrimidin-2-yl]benzoate | 431.5 | 432.1 |
| 170 | 3-(methoxycarbonyl)phenyl | Methyl 3-[5-({[1-(pyridin-2-ylmethyl)piperidin-4-yl]amino}carbonyl)pyrimidin-2-yl]benzoate | 431.5 | 432.1 |

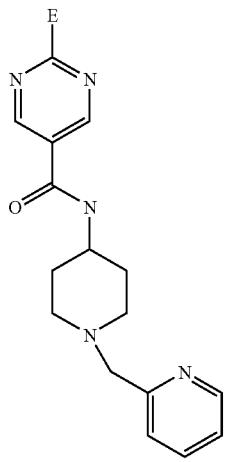

| Ex | E | Name | MS calc (M) | MS obs (M + H) |
|---|---|---|---|---|
| 171 | 2-CF3-phenyl | N-[1-(Pyridin-2-ylmethyl)piperidin-4-yl]-2-[2-(trifluoromethyl)phenyl]pyrimidine-5-carboxamide | 441.5 | 442.1 |
| 172 | 3-CF3-phenyl | N-[1-(Pyridin-2-ylmethyl)piperidin-4-yl]-2-[3-(trifluoromethyl)phenyl]pyrimidine-5-carboxamide | 441.5 | 442.1 |
| 173 | 2-OCF3-phenyl | N-[1-(Pyridin-2-ylmethyl)piperidin-4-yl]-2-[2-(trifluoromethoxy)phenyl]pyrimidine-5-carboxamide | 457.5 | 458.1 |
| 174 | 3-OCF3-phenyl | N-[1-(Pyridin-2-ylmethyl)piperidin-4-yl]-2-[3-(trifluoromethoxy)phenyl]pyrimidine-5-carboxamide | 457.5 | 458.1 |
| 175 | 3-(iPrO2C)-phenyl | Isopropyl 3-[5-({[1-(pyridin-2-ylmethyl)piperidin-4-yl]amino}carbonyl)pyrimidin-2-yl]benzoate | 459.6 | 460.2 |
| 176 | 3-(MeSO2NH)-phenyl | 2-{3-[(Methylsulfonyl)amino]phenyl}-N-[1-(pyridin-2-ylmethyl)piperidin-4-yl]pyrimidine-5-carboxamide | 466.6 | 467.1 |

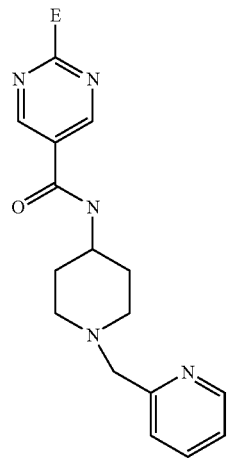

| Ex | E | Name | MS calc (M) | MS obs (M + H) |
|---|---|---|---|---|
| 177 | 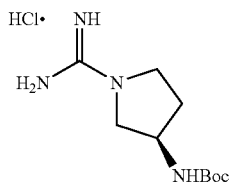 | 2-(3-Fluorophenyl)-N-[1-(pyridin-2-ylmethyl)piperidin-4-yl]pyrimidine-5-carboxamide | 391.5 | 392.1 |

EXAMPLES 78a AND 78b 2-(3-Fluorophenyl)-N-[(3R)-1-(6-methyl-5,6,7,8-tetrahydropyrido[4,3-d]pyrimidin-2-yl)pyrrolidin-3-yl]pyrimidine-5-carboxamide and 2-(3-Fluorophenyl)-N-[(3S)-1-(6-methyl-5,6,7,8-tetrahydropyrido[4,3-d]pyrimidin-2-yl)pyrrolidin-3-yl]pyrimidine-5-carboxamide

Step A: tert-Butyl {(3R)-1-[Amino(imino)methyl]pyrrolidin-3-yl}carbamate hydrochloride

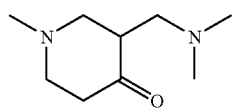

Pyrazolecarboxamidine (7.44 g, 50.7 mmol) was added in one portion to a solution of tert-butyl(3R)-pyrrolidin-2-yl carbamate (9.45 g, 50.7 mmol) in dimethylformamide (50 mL). Diisopropylamine (8.86 mL, 50.7 mmol) was then added dropwise and the reaction mixture was stirred at room temperature over night. The dimethylformamide was evaporated, and dry diethyl ether (150 mL) was added to the oily residue which was stirred until a fine white precipitate formed. The precipitate was separated by filtration to give the title compound in 100% yield. ¹H NMR (DMSO-d6) 1.40 (s, 9H) 2.07 (m, 1H) 3.17 (dd, J=10.2, 4 Hz, 1H) 3.35-4.09 (m, 4H) 4.08 (br m, 1H) 7.33 (br m, 5H).

Step B: 3-[(Dimethylamino)methylene]-1-methylpiperidin-4-one

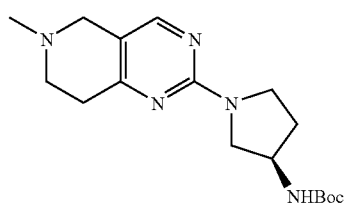

To a solution of 1-methylpiperidin-4-one (10 g, 88 mmol) in toluene (100 mL) was added 1,1-dimethoxy-N,N-dimethylmethanamine (52.7 g, 0.442 mol). The solution was heated to reflux overnight. The solvents were evaporated in vacuo, heptane (100 ml) was added and the solvents evaporated again to give the desired product. NMR indicated that the product was 70-80% pure and it was used in the next step without further purification.

Step C: tert-Butyl [(3R)-1-(6-Methyl-5,6,7,8-tetrahydropyrido[4,3-d]pyrimidin-2-yl)pyrrolidin-3-yl]carbamate

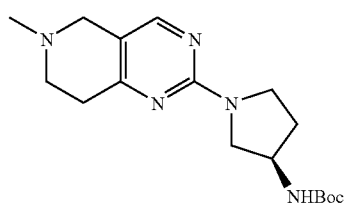

3-[(Dimethylamino)methylene]-1-methylpiperidin-4-one (9.04 g, 53.7 mmol) and tert-butyl {(3R)-1-[amino(imino)methyl]pyrrolidin-3-yl}carbamate hydrochloride (14.2 g, 53.7 mmol) were dissolved in methanol (100 mL) and to this was added dropwise sodium methoxide (9.66 g of a 30% solution in methanol). The reaction mixture was refluxed for 3 hours and then cooled to room temperature. The reaction mixture was then evaporated to dryness, and the residue was treated with water (50 mL). The precipitate was separated by filtration, washed with water (25 mL) and diethyl ether (50 mL) and dried to give the title compound 10.43 g (yield 58%). LCMS (ES+) M+H 334. $^1$H NMR (DMSO-d6) 1.39 (s, 9H) 1.85 (m, 1H) 2.13 (m, 1H) 2.33 (s, 3H) 2.60 (m, 2H) 2.67 (m, 2H) 3.23-3.26 (m, 1H) 3.31-3.37 (m, 3H) 3.40-3.536 (m, 1H) 3.63 (m, 1H) 4.04 (br s, 1H) 7.20 (br s, 1H) 8.04 (s, 1H).

Step D: (3R)-1-(6-Methyl-5,6,7,8-tetrahydropyrido[4,3-d]pyrimidin-2-yl)pyrrolidin-3-amine Trihydrochloride

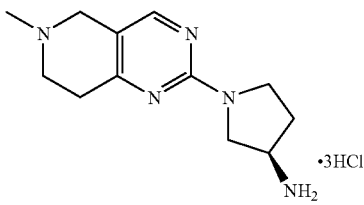

tert-Butyl [(3R)-1-(6-methyl-5,6,7,8-tetrahydropyrido[4,3-d]pyrimidin-2-yl)pyrrolidin-3-yl]carbamate (10.0 g, 30.0 mmol) was dissolved in methanol (40 mL) and cooled to 0° C. To this was added a solution of 4 N hydrochloric acid in dioxane (80 mL). The mixture was allowed to warm to room temperature and then stirred at room temperature for 1 hour and then evaporated to dryness. The residue was boiled with ethanol (100 mL) then cooled to 0° C. and the resulting precipitate was filtered off. This gave the title compound (6.99 g, yield 69%) as a pale pink hygroscopic solid. LCMS (ES+) M+H 234. $^1$H NMR (DMSO-d6) 2.12 (m, 1H) 2.30 (m, 1H) 2.86-2.94 (s+m, 4H) 3.14-3.24 (m, 1H) 3.37-3.46 (m, 1H) 3.56-3.77 (br m, 6H) 3.78 (br m, 1H) 4.13 (dd, J=14.6, 8.3 Hz, 1H) 4.35 (d, J=14.0 Hz, 1H) 8.28 (s, 1H) 8.52 (br s, 3H) 11.71 (br s, 1H). LRMS M+H 234.

Step E: 3-Fluorobenzenecarboximidamide

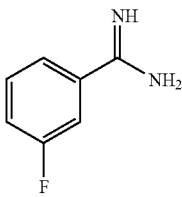

Dry HCl gas was bubbled through a solution of 3-fluorobenzonitrile (50 g, 0.41 mol) in ethanol (500 ml) with ice cooling for 4-5 hours and then at 40° C. for 4 h. The reaction mixture was then stirred at room temperature overnight. Dry HCl gas was again bubbled through at 40° C. for 8 hours and then the reaction was stirred at this temperature overnight. The reaction was concentrated, stirred with dry diethyl ether (~300 ml), filtered, washed with dry diethyl ether (2×200 mL) and dried. It was then taken up in ethanol (500 mL), saturated with liquid ammonia at −70° C. and stirred at this temperature overnight. It was concentrated to obtain the desired compound, yield 56 g (98.9%).

Step F: Methyl 2-(3-fluorophenyl)pyrimidine-5-carboxylate

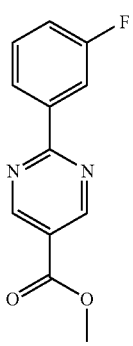

To a solution of methyl 3,3-dimethoxypropionate (304 g, 2.05 mol) in dimethoxyethane (1.5 L) was added methyl formate (580 g, 9.44 mol). Sodium hydride (98.5 g, 60% suspension in mineral oil, 2.46 mol) was added portion-wise and the mixture was stirred at 50° C. for 5 hours and then at room temperature overnight. Diethyl ether (1.5 L) was added and the reaction was filtered under an atmosphere of nitrogen. The solid residue was washed with diethyl ether (300 mL ×2) and dried to give 200 g (68.9%) of [methyl-2-(dimethoxymethyl)-3-(hydroxyl-kappaO)acrylatato]sodium. A mixture of this compound (63.5 g, 0.32 mol), 3-fluorobenzenecarboximidamide (38 g, 0.27 mol) and dimethylformamide (400 mL) was heated at 100° C. for 2 h. After this time the reaction was cooled to room temperature and water (400 mL) was added. The reaction was filtered and the residue was washed with water (100 mL x2) and dried to give 37 g (yield 59%) of methyl 2-(3-fluorophenyl)pyrimidine-5-carboxylate.

Step G: 2-(3-Fluorophenyl)pyrimidine-5-carboxylic acid

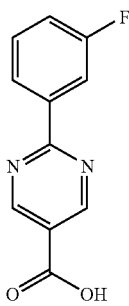

To a solution of methyl 2-(3-fluorophenyl)pyrimidine-5-carboxylate (45 g, 0.19 ml) in a 1:1 mixture of tetrahydrofuran and ethanol (120 mL) was added Li(OH).H$_2$O (12.2 g, 0.29 mol) dissolved in water (120 mL) and the reaction mixture was stirred at room temperature overnight. The reaction was concentrated under reduced pressure, dissolved in water (500 mL), acidified with 1N aqueous HCl and filtered. The residue was washed with water (100 mL×3) and dried to give 37 g (yield 89.5%) of 2-(3-fluorophenyl)pyrimidine-5-carboxylic acid. $^1$H NMR (DMSO-d6) 7.49 (m, 1H) 7.67 (m, 1H) 8.18 (m, 1H) 8.34 (m, 1H) 9.34 (s, 2H). LRMS (ES+) M+H 219.

Step H: 2-(3-Fluorophenyl)-N-[(3R)-1-(6-methyl-5,6,7,8-tetrahydropyrido[4,3-d]pyrimidin-2-yl)pyrrolidin-3-yl]pyrimidine-5-carboxamide (Example 78a)

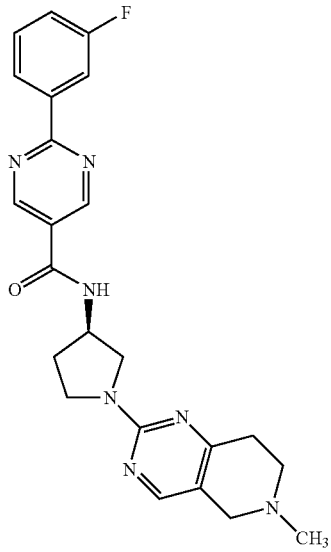

(3R)-1-(6-Methyl-5,6,7,8-tetrahydropyrido[4,3-d]pyrimidin-2-yl)pyrrolidin-3-amine trihydrochloride (4.97 g, 11.0 mmol), 2-(3-fluorophenyl)pyrimidine-5-carboxylic acid (2.4 g, 11.0 mmol), N-ethyl-N'-(3-aminopropyl)carbodiimide.HCl (2.32 g, 12.1 mmol), 1-hydroxy-7-azabenzotriazole (0.15 g, 1.1 mmol) and N,N-diisopropylethylamine (5.75 mL, 33.0 mmol) were suspended in dichloromethane (50 mL) and stirred over night at room temperature. The solvents were evaporated in vacuo and the residue purified by column chromatography on silica, eluting with ethyl acetate:methanol in a ratio 3:1 to give the product as a sticky yellow solid (6.5 g). This was stirred in a mixture of ethyl acetate (25 mL) and methanol (25 mL) and the resulting precipitate was filtered off, washed with diethyl ether and dried to give the product 1.9 g. The mother liquors were evaporated in vacuo and the residue stirred in diethyl ether (100 mL). The solvent was decanted off yielding an off white solid which was recrystallised from ethanol (50 mL) to give another batch of the desired product (0.5 g). The combined batches were stirred in methanol (50 mL) and brought to pH>8 with 7N ammonia in methanol. The solvents were evaporated off and the residue was purified using chromatography on silica eluting with ethyl acetate and then ethyl acetate:7N ammonia in methanol 1:1 after which the NMR indicated the presence of ammonium chloride in the product. The product was then purified using ion exchange chromatography on DOWEX 50Wx4. The product was applied to the column in a solution in methanol:dimethyl sulphoxide 1:1, the column was washed with water and then eluted with 7N ammonia in methanol to give the desired product (1.7 g). $^1$H NMR (DMSO-d6) 2.08 (m, 1H) 2.27 (m, 1H) 2.35 (s, 3H) 2.64 (m, 2H) 2.71 (m, 2H) 3.35 (m, 2H) 3.58 (m, 2H) 3.66 (m, 1H) 3.82 (m, 1H) 4.60 (m, 1H) 7.46 (m, 1H) 7.64 (m, 1H) 8.09 (s, 1H) 8.16 (m, 1H) 8.31 (m, 1H) 9.00 (d, J=6.7 Hz, 1H), 9.29 (s, 2H).

2-(3-Fluorophenyl)-N-[(3S)-1-(6-methyl-5,6,7,8-tetrahydropyrido[4,3-d]pyrimidin-2-yl)pyrrolidin-3-yl]pyrimidine-5-carboxamide (Example 78b)

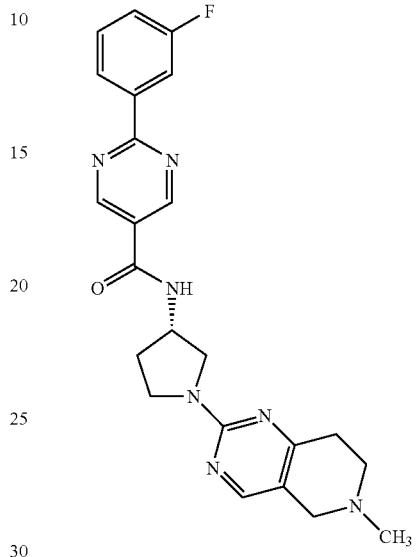

This compound was prepared in the same way as Example 78a starting from tert-butyl (3S)-pyrrolidine-3-yl carbamate.

Biological Data

Fluoresecence Intensity h-PGDSTBA Enzyme Assay

Prostaglandin D Synthase (PGDS) converts the substrate prostaglandin $H_2$ ($PGH_2$) to prostaglandin $D_2$. The depletion of $PGH_2$ was measured via an Fe(II) reduction of the remaining $PGH_2$ to malondialdehyde (MDA) and 12-HHT. The enzyme assay is based on the quantitative formation of a fluorescent complex from the non-fluorescent compounds MDA and 2-thiobarbituric acid (TBA), substantially as described in U.S. patent application publication US-2004/152148 by Lambalot.

The enzyme assay (31 μls) contained 100 mM Tris base pH 8.0, 100 μM $MgCl_2$, 0.1 mg/ml IgG Rabbit serum, 5.0 μM PGH2 (Cayman; ethanol solution, #17020), 2.5 mM L-Glutathione (Sigma; reduced form #G4251), 1:175,000 human recombinant H-PGDS (from 1 mg/ml), 0.5% DMSO and inhibitor (varying concentration). Three μls of diluted inhibitor (dissolved in DMSO) was plated into a 384-well assay plate followed by a 25 μl addition of an enzyme solution containing h-PGDS, Tris, $MgCl_2$, IgG and L-Glutathione. After preincubation of inhibitor and enzyme solution for 10 minutes at room temperature, the reaction was initiated with a 3 μl addition of substrate solution in 10 mM HCl. The reaction was terminated after 42 second by the addition (3 μl) of stop buffer containing $FeCl_2$ and citric acid. After addition of 45.5 μls of TBA plates were heated for one hour in a 70° C. oven. Plates were cooled at room temperature overnight and read on a plate reader the next day with excitation @ 530 nm and emission @ 565 nm. $IC_{50}$'s of inhibitors were calculated with a 4-parameter fit using 11 inhibitor concentrations in duplicate with 3-fold serial dilutions. Controls on each plate included no inhibitor (zero % effect) and an inhibitor 10-fold in excess of its' $IC_{50}$ (100% effect). The highest inhibitor concentration tested was typically 1 μM.

Examples 623 onwards were tested in a slightly modified assay: The enzyme assay (30 µls during biological process) contained 100 mM Trizma pH 8.0, 100 µM $MgCl_2$, 0.1 mg/ml IgG Rabbit serum, 5.0 µM PGH2 (Cayman; ethanol solution, #17020), 2.5 mM L-Glutathione (Sigma; reduced form #G4251), 1:40,000 human recombinant H-PGDS (from 1 mg/ml), 0.5% DMSO and inhibitor (varying concentration). 3 µls of diluted inhibitor (dissolved in DMSO) was plated into a 384-well assay plate followed by a 24 µl addition of an enzyme solution containing h-PGDS, Trizma, $MgCl_2$, IgG and L-Glutathione. After pre-incubation of inhibitor and enzyme solution for 10 minutes at room temperature, the reaction was initiated with a 3 µl addition of substrate solution in 10 mM HCl. The reaction was terminated after 40 second by the addition of 3 µl stop buffer containing $FeCl_2$ and citric acid. After addition of 45 µls of TBA plates were heated for one hour in a 70° C. oven. Plates were cooled at room temperature overnight and read on a plate reader the next day with excitation @ 530 nm and emission @ 560 nm. $IC_{50}$'s of inhibitors were calculated with a 4-parameter fit using 11 inhibitor concentrations in duplicate with ½log serial dilutions. Controls on each plate included no inhibitor (zero % effect) and an inhibitor 500-fold in excess of its' $IC_{50}$ (100% effect). The highest inhibitor concentration tested was typically 10 µM.

Table II shows the $IC_{50}$ values thus obtained.

TABLE II

| Example | $IC_{50}$ (nM) |
| --- | --- |
| 1 | 162 |
| 2 | 67.4 |
| 3 | 14.1 |
| 4 | 302 |
| 5 | 8.02 |
| 6 | 6.54 |
| 7 | 30.4 |
| 8 | 0.461 |
| 9 | 0.275 |
| 10 | 2 |
| 11 | 0.381 |
| 12 | 0.428 |
| 13 | 6.34 |
| 14 | 0.483 |
| 15 | 1000 |
| 16 | 219 |
| 17 | 19.3 |
| 18 | 16.4 |
| 19 | 1000 |
| 20 | 1000 |
| 21 | 992 |
| 22 | 1000 |
| 23 | 1000 |
| 24 | 1000 |
| 25 | 0.373 |
| 26 | 0.136 |
| 27 | 0.166 |
| 28 | 4.45 |
| 29 | 11.4 |
| 30 | 6.55 |
| 31 | 7.68 |
| 32 | 8.91 |
| 33 | 15.5 |
| 34 | 6.46 |
| 35 | 0.62 |
| 36 | 4.54 |
| 37 | 7.07 |
| 38 | 6.71 |
| 39 | 4.44 |
| 40 | 3.02 |
| 41 | 10.2 |
| 42 | 54.8 |
| 43 | 35 |
| 44 | 16.2 |
| 45 | 14.2 |
| 46 | 23.8 |
| 47 | 10.2 |
| 48 | 29.6 |
| 49 | 6.26 |
| 50 | 9.55 |
| 51 | 10 |
| 52 | 0.457 |
| 53 | 59.2 |
| 54 | 6.13 |
| 55 | 45.4 |
| 56 | 14.2 |
| 57 | 11.4 |
| 58 | 2.08 |
| 59 | 8.16 |
| 60 | 1.02 |
| 61 | 0.58 |
| 62 | 0.489 |
| 63 | 0.509 |
| 64 | 0.16 |
| 65 | 0.335 |
| 66 | 0.355 |
| 67 | 30 |
| 68 | 0.373 |
| 69 | 3.59 |
| 70 | 0.962 |
| 71 | 0.355 |
| 72 | 30 |
| 73 | 1.84 |
| 74 | 3.2 |
| 75 | 18.3 |
| 76 | 0.595 |
| 77 | |
| 78 | 0.379 |
| 79 | 0.346 |
| 80 | 0.211 |
| 81 | 0.219 |
| 82 | 0.658 |
| 83 | 1.18 |
| 84 | 0.987 |
| 85 | 2.34 |
| 86 | 6.43 |
| 87 | 6.57 |
| 88 | 1.58 |
| 89 | 0.147 |
| 90 | 0.808 |
| 91 | 2.8 |
| 92 | 2.87 |
| 93 | |
| 94 | 1.41 |
| 95 | |
| 96 | 3.54 |
| 97 | 3.83 |
| 98 | 1.82 |
| 99 | 2.65 |
| 100 | 4.47 |
| 101 | 0.237 |
| 102 | |
| 103 | 0.815 |
| 104 | 0.706 |
| 105 | 0.364 |
| 106 | 2.98 |
| 107 | |
| 108 | |
| 109 | |
| 110 | |
| 111 | |
| 112 | |
| 113 | 1010 |
| 114 | |
| 115 | |
| 116 | |
| 117 | |
| 118 | |
| 119 | 9460 |
| 120 | |
| 121 | |
| 122 | |

TABLE II-continued

| Example | IC$_{50}$ (nM) |
|---|---|
| 123 | |
| 124 | |
| 125 | 270 |
| 126 | |
| 127 | |
| 128 | |
| 129 | |
| 130 | |
| 131 | |
| 132 | |
| 133 | |
| 134 | |
| 135 | |
| 136 | |
| 137 | |
| 138 | |
| 139 | |
| 140 | |
| 141 | |
| 142 | 64 |
| 143 | |
| 144 | |
| 145 | |
| 146 | |
| 147 | |
| 148 | |
| 149 | |
| 150 | |
| 151 | |
| 152 | |
| 153 | |
| 154 | |
| 155 | |
| 156 | |
| 157 | |
| 158 | |
| 159 | 2040 |
| 160 | |
| 161 | |
| 162 | |
| 163 | |
| 164 | |
| 165 | |
| 166 | |
| 167 | |
| 168 | |
| 169 | |
| 170 | |
| 171 | |
| 172 | |
| 173 | |
| 174 | |
| 175 | |
| 176 | 2700 |
| 177 | |
| 78a | 13 |
| 78b | 1 |
| 81a | 0.27 |
| 81b | 0.46 |
| 82a | 1.92 |
| 82b | 0.58 |

The invention claimed is:

1. A compound of Formula (Ia):

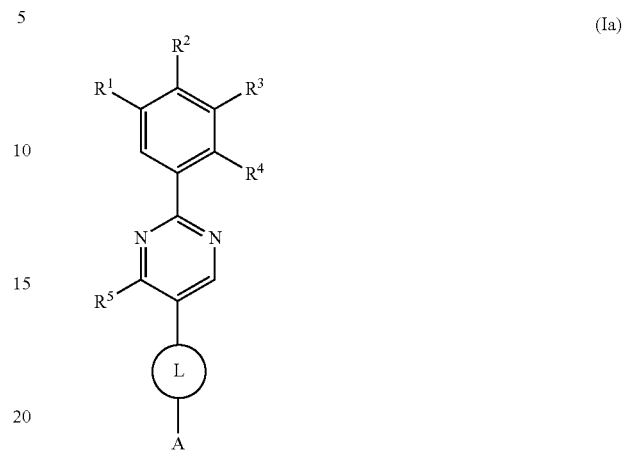

or a pharmaceutically acceptable salt thereof, wherein:

$R^1$, $R^3$ and $R^4$ are independently H, F, Cl, —CHF$_2$, —CF$_3$, —OH, —CH$_2$OH, —CH$_2$CH$_2$OH, —C≡N, —CH$_2$C≡N, —CH$_2$CH$_2$C≡N, C$_1$-C$_5$ alkyl, C(O)OR$^{16}$, —NC(O)R$^{16}$, —NS(O)$_2$R$^{16}$, —C(O)R$^{16}$, or —OCH$_3$;

$R^{16}$ is C$_1$-C$_5$ alkyl;

$R^2$ is H or F;

$R^5$ is H, —NH$_2$, —OH or —CH$_3$;

L is —C(O)NH—, —NHC(O)— or —CH$_2$NHC(O)—; and

A is selected from the group consisting of:

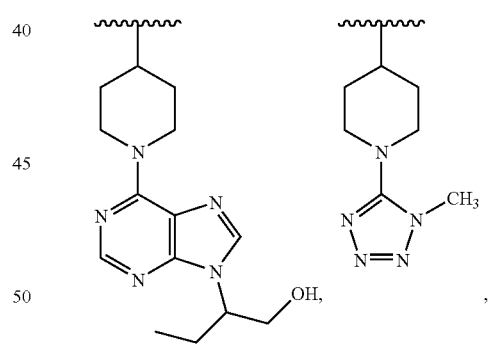

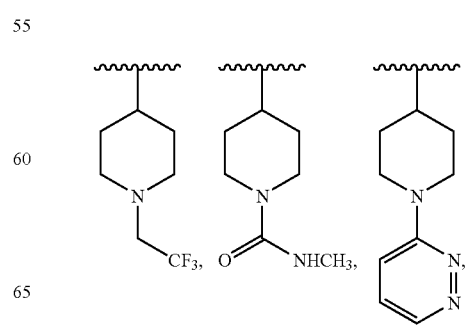

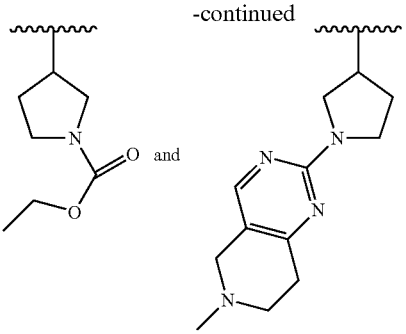

2. A compound of claim 1, or a pharmaceutically acceptable salt thereof, wherein the compound is:

ethyl 3-(2-(3-fluorophenyl)pyrimidine-5-carboxamido)pyrrolidine-1-carboxylate;

2-(3-fluorophenyl)-N-{1-[(methylamino)carbonyl]piperidin-4-yl}pyrimidine-5-carboxamide;

2-(3-fluorophenyl)-N-[1-(6-methyl-5,6,7,8-tetrahydropyrido[4,3-d]pyrimidin-2-yl)-pyrrolidin-3-yl]pyrimidine-5-carboxamide; or 2-(3-fluorophenyl)-N-[1-(2,2,2-trifluoroethyl)piperidin-4-yl]pyrimidine-5-carboxamide.

3. A pharmaceutical composition comprising a compound claim 1, or a pharmaceutically acceptable salt thereof, and a pharmaceutically acceptable excipient.

4. A method of treating asthma, in a subject in need of such treatment, comprising administering to the subject a therapeutically effective amount of a compound of claim 1, or a pharmaceutically acceptable salt thereof.

5. A pharmaceutical composition comprising a compound of claim 1, or a pharmaceutically acceptable salt thereof, and a second pharmacologically active compound.

* * * * *